(12) United States Patent
Souza et al.

(10) Patent No.: US 9,850,254 B2
(45) Date of Patent: *Dec. 26, 2017

(54) SYNTHETIC PROCESS FOR PREPARATION OF MACROCYCLIC C1-KETO ANALOGS OF HALICHONDRIN B AND INTERMEDIATES USEFUL THEREIN INCLUDING INTERMEDIATES CONTAINING-SO$_2$-(P-TOLYL) GROUPS

(71) Applicant: ALPHORA RESEARCH INC., Mississauga, Ontario (CA)

(72) Inventors: Fabio E. S. Souza, Mississauga (CA); Alena Rudolph, Puslinch (CA); Dino Alberico, Mississauga (CA); Robert Jordan, Rockwood (CA); Ming Pan, Mississauga (CA); Boris Gorin, Oakville (CA)

(73) Assignee: Sandoz AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/901,481

(22) PCT Filed: May 30, 2014

(86) PCT No.: PCT/CA2014/050504
§ 371 (c)(1),
(2) Date: Dec. 28, 2015

(87) PCT Pub. No.: WO2015/000070
PCT Pub. Date: Jan. 8, 2015

(65) Prior Publication Data
US 2016/0137661 A1    May 19, 2016

Related U.S. Application Data

(60) Provisional application No. 61/842,467, filed on Jul. 3, 2013.

(51) Int. Cl.

| C07D 311/00 | (2006.01) |
|---|---|
| C07D 493/04 | (2006.01) |
| C07D 407/14 | (2006.01) |
| C07D 493/22 | (2006.01) |
| C07D 307/20 | (2006.01) |
| C07D 307/28 | (2006.01) |
| C07D 407/06 | (2006.01) |

(52) U.S. Cl.
CPC ......... *C07D 493/04* (2013.01); *C07D 307/20* (2013.01); *C07D 307/28* (2013.01); *C07D 407/06* (2013.01); *C07D 407/14* (2013.01); *C07D 493/22* (2013.01)

(58) Field of Classification Search
CPC .................................................. C07D 493/04
See application file for complete search history.

(56) References Cited

U.S. PATENT DOCUMENTS 6,214,865 B1    4/2001 Littlefield et al.
9,278,979 B2*   3/2016 Souza .................. C07D 407/14

FOREIGN PATENT DOCUMENTS

WO    WO 99/65894 A1       12/1999
WO    WO 2013/142999 A1    10/2013

OTHER PUBLICATIONS

Dong et al., "New Syntheses of E7389 C14—C35 and Halichondrin C14—C38 Building Blocks: Reductive Cyclization and Oxy-Michael Cyclization Approaches," J. Am. Chem. Soc., Jun. 10, 2009, pp. 15642-15646, vol. 131, 2009.
International Search Report issued in PCT/CA2014/050504 mailed Jul. 24, 2014.
Rudolph et al., "Early introduction of the amino group to the C27—C35 building block of Eribulin," Tetrahedron Letters, Oct. 22, 2013, pp. 7059-7061, vol. 54, 2013.
Zheng et al., "Macrocyclic ketone analogues of halichondrin B," Bioorg. Med. Chem. Lett., Sep. 21, 2004, pp. 5551-5554, vol. 14, 2004.

* cited by examiner

*Primary Examiner* — Nizal Chandrakumar
(74) *Attorney, Agent, or Firm* — Arent Fox LLP

(57) ABSTRACT

Disclosed is a compound of formula 1, or a pharmaceutically acceptable salt thereof, where $R^1$, $R^2$, $R^3$, $R^4$, $R^5$, $R^6$, $R^7$, $R^{7'}$, $R^8$, $R^9$, $R^{10}$, $R^{11}$, $R^{12}$ and $R^{13}$ are as disclosed herein. Also, disclosed is a process for the preparation of the compound of formula 1, or a pharmaceutically acceptable salt thereof, and intermediates used therein. The compound of formula 1 can be used in the preparation of halichondrin analogs, such as Eribulin; and a process for its preparation from the compound of formula 1 is also disclosed.

14 Claims, No Drawings

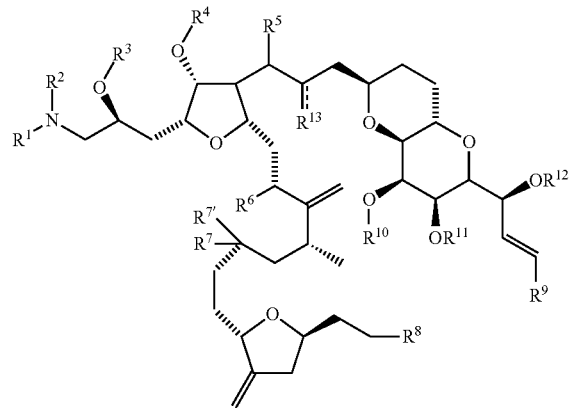

SYNTHETIC PROCESS FOR PREPARATION OF MACROCYCLIC C1-KETO ANALOGS OF HALICHONDRIN B AND INTERMEDIATES USEFUL THEREIN INCLUDING INTERMEDIATES CONTAINING-$SO_2$-(P-TOLYL) GROUPS

CROSS-REFERENCE TO RELATED APPLICATION

This application is a National Stage entry of International Application No. PCT/CA2014/050504, filed May 30, 2014, which claims the benefit of and priority to U.S. provisional patent application Ser. No. 61/842,467 filed Jul. 3, 2013, under the title SYNTHETIC PROCESS FOR PREPARATION OF MACROCYCLIC C1-KETO ANALOGS OF HALICHONDRIN B AND INTERMEDIATES USEFUL THEREIN INCLUDING INTERMEDIATES CONTAINING—$SO_2$-(p-TOLYL) GROUPS. The content of the above patent application is hereby expressly incorporated herein by reference into the detailed description hereof.

FIELD

The specification relates to a synthetic process for preparation of macrocyclic C1-keto analogs of Halichondrin B, their salts and intermediates useful for their preparation.

BACKGROUND

Halichondrins have been disclosed as having anti-cancer and antimitotic activity (*Chem. Rev.* 2009, 109, 3044-3079, incorporated herein by reference). In particular, Halichondrin B has been reported as a potent anticancer agent that was first isolated from the marine sponge *Halichondria okadai* (U.S. Pat. No. 5,436,238; *Tetrahedron Lett.* 1994, 35, 9435 and WO 1993/017690 A1, all incorporated herein by reference). It was further reported that analogs of Halichondrin B bearing only macrocyclic fragment of its molecule (C1-C30 fragment) and having a ketone function instead of ester at C1 position demonstrate anticancer activity similar to Halichondrin B (Bioorg. Med. Chem. Lett., 2000, 10, 1029 and *Bioorg. Med. Chem. Lett.*, 2004, 14, 5551) It was established that such macrocyclic fragment is responsible for induction of mitotic blocks in cancer cells via disruption of tubulin polymerization process that triggers apoptosis of cancerous cells and stops their proliferation (Cancer Res., 2004, 64, 5760 and Mol. Canc. Ther., 2008, 7, 2003). Eribulin mesylate, a macrocyclic C1-keto analog of Halichondrin B, has been reported as having potent anticancer properties (WO 1999/065894 A1, incorporated herein by reference). Eribulin is marketed under the trade name Halaven, and it is also known as E7389, B1939 and ER-086526.

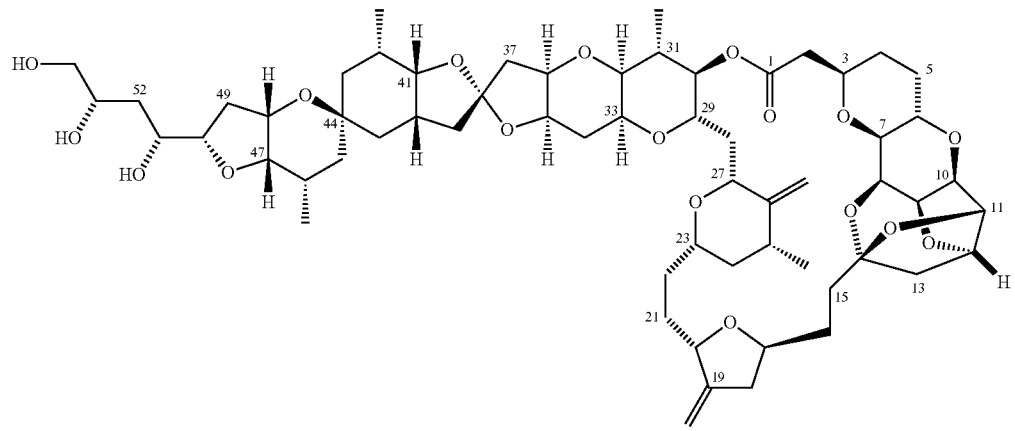

Halichondrin B

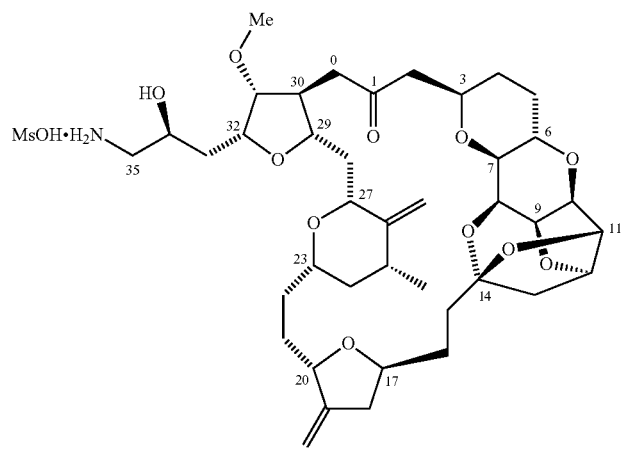

Eribulin mesylate

The synthetic approach described (U.S. Pat. No. 6,214,865; WO 2009/124237 A1, *Bioorg. Med. Chem. Lett.*, 2004, 14, 5551 and *J. Am. Chem. Soc.* 2009, 131, 15642, all incorporated herein by reference) involves introduction of nitrogen in the C27-C35 fragment of Eribulin after assembly of the macrocycle. Such an approach can add synthetic steps to the later stages of the synthesis, after the building blocks corresponding to the C1-C13 and C14-C26 fragments have been introduced. The synthesis of those fragments is long and complex; and every additional step in the synthesis can imply an increase in manufacturing costs. In addition, due to the cytotoxic nature of Eribulin, late introduction of the nitrogen results in a greater number of steps that can require special safety containment, which can limit throughput and can also increase the cost of producing the active pharmaceutical ingredient (API).

There is a need in the art for a compound that can be used in process for preparation of Eribulin and other macrocyclic C1-keto analogs of Halichondrin B and their salts. In addition, there is a need in the art for a compound and a process that can help to improve the convergence of the synthetic route for preparation of Eribulin and other macrocyclic C1-keto analogs of Halichondrin B and their salts, and therefore, can also help to reduce the amount of C1-C13 and C14-C26 fragments required. Further, there is a need in the art for a compound that can help to reduce the number of steps that can require safety containment for preparation of Halichondrin and its analogs. Moreover, there is a need in the art for a process for preparation of such a compound.

PCT/CA2013/050254, incorporated herein by reference, discloses compounds and routes for the preparation of eribulin and other macrocyclic C1-keto analogs of halichondrin B and their salts.

In addition to the above, it has been found that the synthetic processes for making C27-C35 fragment and related intermediates can involve intricate chemistry that can require rigorous chromatographic purification to attain desired quality acceptable in pharmaceutical manufacture. This can lead to substantial losses of materials to chromatographic purification, thus lowering yields from the manufacturing processes. Consequently, there is also a need in the art for an intermediate that can be used in the process for preparation eribulin and other C1-keto analogs of halichondrin B and their salts, that can assist in purification of the intermediate and other compounds obtained using the intermediate. Consequently, this can also lead to an increase in product quality and quantity of the intermediate, eribulin and other C1-keto analogs of Halichondrin B and their salts, while also leading to a reduction in cost of the overall manufacturing process.

SUMMARY OF THE INVENTION

In one aspect, the specification relates to a compound of formula 1, or a pharmaceutically acceptable salt thereof,

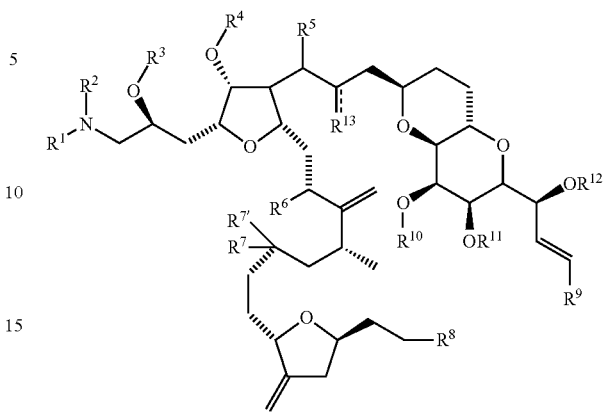

wherein $R^1$, $R^2$, $R^3$, $R^4$, $R^5$, $R^6$, $R^7$, $R^{7'}$, $R^8$, $R^9$, $R^{10}$, $R^{11}$, $R^{12}$ and $R^{13}$ are as described herein.

In another aspect, the specification relates to a compound of formula 2, or a pharmaceutically acceptable salt thereof,

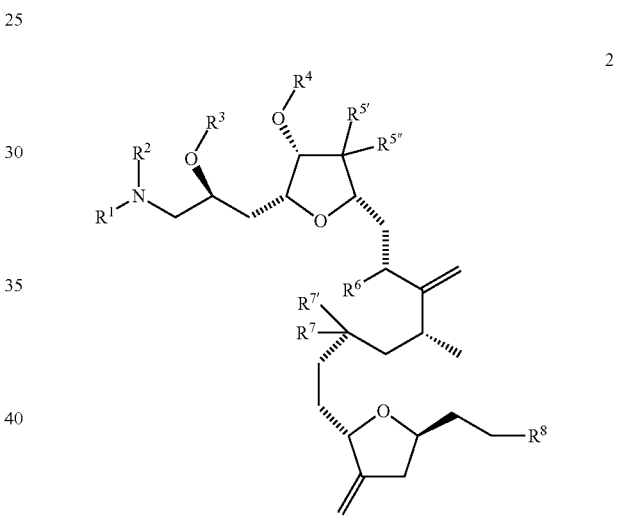

wherein $R^1$, $R^2$, $R^3$, $R^4$, $R^{5'}$, $R^{5''}$, $R^6$, $R^7$, $R^{7'}$ and $R^8$ are as described herein.

In a further aspect, the specification relates to a compound of formula 5, or a pharmaceutically acceptable salt thereof,

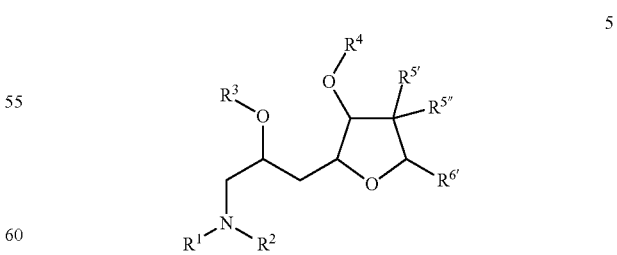

wherein $R^1$, $R^2$, $R^3$, $R^4$, $R^{5'}$, $R^{5''}$ and $R^{6'}$ are as described herein.

In still another aspect, the specification relates to a process for preparation of analogs of halichondrin, including eribulin, from the compound of formula 1, 2 or 5.

In a still further aspect, the specification relates to a process for preparation of the compound of formula 1, 2 or 5, or a pharmaceutically acceptable salt thereof.

DESCRIPTION

As described above, in one aspect the specification relates to a compound of formula 1, or a pharmaceutically acceptable salt thereof:

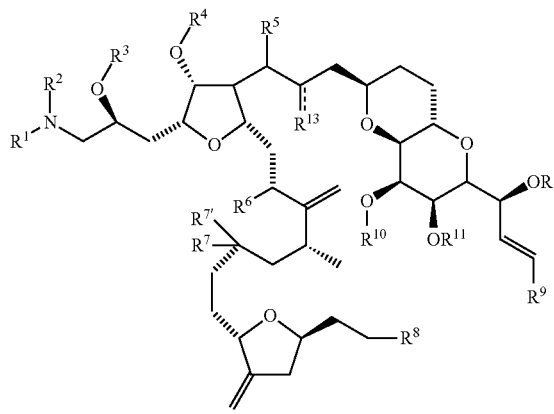

1 wherein
R$^1$ and R$^2$ each independently is H, a silyl group, an acyl group, a sulfonyl group or an alkoxycarbonyl group; or one of R$^1$ and R$^2$ is absent and the other R$^1$ or R$^2$ together with the nitrogen atom to which it is attached form an azide;

R$^3$ is H or an alcohol protecting group;

or R$^3$ and one of R$^1$ and R$^2$ together form —C(═O)—, —C(═O)—C(═O)— or —C(R$^{14}$)(R$^{15}$)—, wherein R$^{14}$ and R$^{15}$ each independently is H or a hydrocarbon, the hydrocarbon optionally having one or more heteroatoms;

R$^4$ is H, C$_{1-3}$ alkyl, C$_{1-3}$ haloalkyl or an alcohol protecting group;

R$^5$ is H or —SO$_2$(p-tolyl), wherein p-tolyl is —(C$_6$H$_4$)—CH$_3$, with the —CH$_3$ at the para-position;

R$^6$ is OR$^{16}$, wherein R$^{16}$ is H or an alcohol protecting group;

R$^7$ and R$^{7'}$ together form a ═O or a protected geminal diol, or one of R$^7$ and R$^{7'}$ is H and the other is a leaving group or a functional group that can be converted into a leaving group;

or R$^6$ and one of R$^7$ and R$^{7'}$ together form —O—, and the other R$^7$ or R$^{7'}$ is H;

R$^8$ is —C(═O)R$^{17}$ or —CH$_2$OR$^{18}$; wherein

R$^{17}$ is H or OR$^{19}$, wherein R$^{19}$ is H or a hydrocarbon, the hydrocarbon optionally having one or more heteroatoms;

R$^{18}$ is H or an alcohol protecting group;

R$^9$ is a halide or a sulfonate;

or R$^8$ and R$^9$ together form —C(═O)— or —CH(OR$^{20}$)—; wherein R$^{20}$ is H or an alcohol protecting group;

R$^{10}$, R$^{11}$ and R$^{12}$ each independently is H or an alcohol protecting group;

----- (representing the bond between R$^{13}$ and the carbon-backbone of molecule 1) is a single or double bond; and R$^{13}$ is ═O or —OR$^{21}$, wherein R$^{21}$ is H or an alcohol protecting group.

In one embodiment, the compound of formula 1 has the structure of formula 1a.

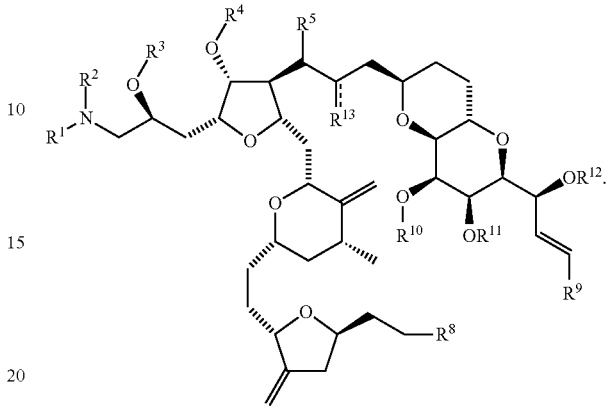

1a where R$^1$, R$^2$, R$^3$, R$^4$, R$^5$, R$^8$, R$^9$, R$^{10}$, R$^{11}$, R$^{12}$, R$^{13}$ and ----- are as described above.

In another aspect, the specification relates to a compound of formula 2, or a pharmaceutically acceptable salt thereof

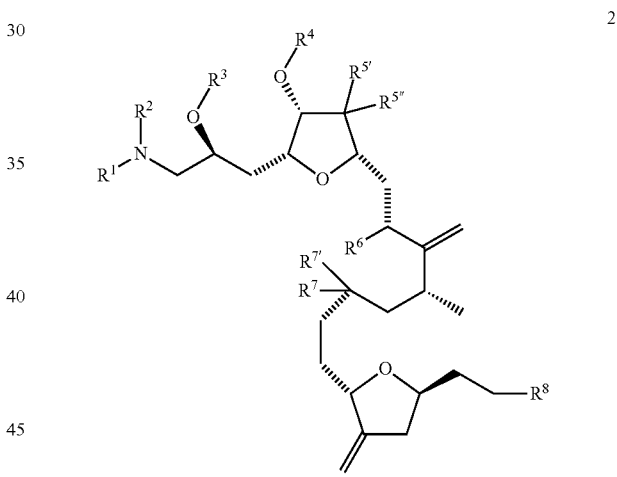

2 wherein
R$^1$ and R$^2$ each independently is H, a silyl group, an acyl group, a sulfonyl group or an alkoxycarbonyl group; or one of R$^1$ and R$^2$ is absent and the other R$^1$ or R$^2$ together with the nitrogen atom to which it is attached form an azide;

R$^3$ is H or an alcohol protecting group;

or R$^3$ and one of R$^1$ and R$^2$ together form —C(═O)—, —C(═O)—C(═O)— or —C(R$^{14}$)(R$^{15}$)—, wherein R$^{14}$ and R$^{15}$ each independently is H or a hydrocarbon, the hydrocarbon optionally having one or more heteroatoms;

R$^4$ is H, C$_{1-3}$ alkyl or C$_{1-3}$ haloalkyl, or an alcohol protecting group;

one of R$^{5'}$ and R$^{5''}$ is H and the other is —CH$_2$SO$_2$-(p-tolyl), or R$^{5'}$ and R$^{5''}$ taken together form ═CH—SO$_2$-(p-tolyl), wherein p-tolyl is —(C$_6$H$_4$)—CH$_3$, with the —CH$_3$ at the para-position;

R$^6$ is OR$^{16}$, wherein R$^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —CH$_2$O$R^{18}$; wherein $R^{17}$ is H or O$R^{19}$, wherein $R^{19}$ is H or a hydrocarbon, the hydrocarbon optionally having one or more heteroatoms;

$R^{18}$ is H or an alcohol protecting group.

In one embodiment, the compound of formula 2 has the structure of formula 2a.

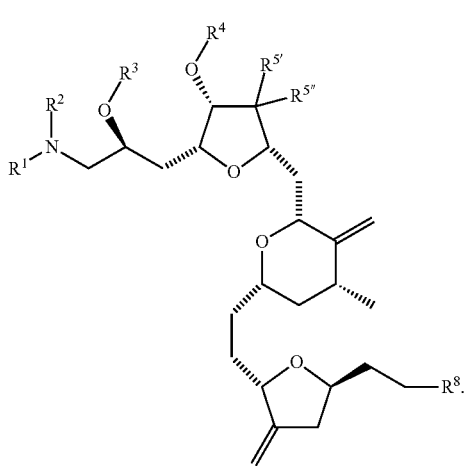

2a

In a further aspect, the specification relates to a compound of formula 5, or a pharmaceutically acceptable salt thereof,

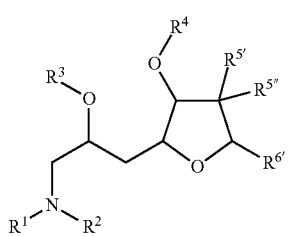

5 wherein, $R^1$ and $R^2$ each independently is H, a silyl group, an acyl group, a sulfonyl group or an alkoxycarbonyl group; or one of $R^1$ and $R^2$ is absent and the other $R^1$ or $R^2$ together with the nitrogen atom to which it is attached form an azide;

$R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms;

$R^4$ is H, $C_{1-3}$ alkyl or $C_{1-3}$ haloalkyl or an alcohol protecting group;

one of $R^{5'}$ and $R^{5'''}$ is H and the other-CH$_2$SO$_2$-(p-tolyl), or $R^{5'}$ and $R^{5'''}$ taken together form =CH—SO$_2$-(p-tolyl), wherein p-tolyl is —(C$_6$H$_4$)—CH$_3$, with the —CH$_3$ at the para-position;

$R^{6'}$ is —CH$_2$—CH=C$R^{29}R^{29'}$, —CH$_2$—CH(O$R^{26}$)—CH(O$R^{26}$)$R^{29}$, —CH$_2$C(=O)—$R^{25}$ or —CH$_2$—CH$_2$—O—$R^{26}$, wherein $R^{29}$ and $R^{29'}$ each independently is H or a hydrocarbon, the hydrocarbon optionally having one or more heteroatoms;

$R^{25}$ is H or O$R^{27}$, wherein $R^{27}$ is H or a hydrocarbon, the hydrocarbon optionally having one or more heteroatoms;

each $R^{26}$ independently is H or an alcohol protecting group.

In one embodiment, the compound of formula 5 has the structure of formula 5a.

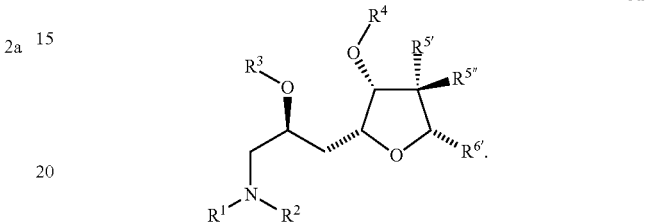

5a

The pharmaceutically acceptable salts as disclosed herein are not particularly limited and should be known to a skilled worker, or can be determined. There are no particular limitations on the pharmaceutically acceptable salt so long as eribulin or an intermediate, and salt are formed, whether inorganic acid salt or organic acid salt. For example and without limitation, the salt can be hydrochloric acid salt, sulfuric acid salt, citrate, hydrobromic acid salt, hydroiodic acid salt, nitric acid salt, bisulfate, phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt (also referred to as mesylic acid salt), ethanesulfonic acid salt, benzenesulfonic acid salt, p-toluenesulfonic acid salt, pamoic acid salt (pamoate), and so on. Preferable among these are hydrochloric acid salt, sulfuric acid salt, acetic acid salt, phosphoric acid salt, citrate, and methanesulfonic acid salt, and most preferable of all is methanesulfonic acid salt. That is, the preferable active compound of the present invention is eribulin mesylate. Eribulin or its pharmaceutically acceptable salt is the compound or its salt as recorded in PCT International Publication WO 99/065894 or U.S. Pat. No. 6,214,865 (the contents of which are incorporated herein by reference).

The term "silyl group" as used herein is not particularly limited, and should be known to a person of skill in the art. In one embodiment, for example and without limitation, the silyl group refers to the general formula "R$_3$Si—", where each R is a hydrocarbon and can be the same or different. The silyl group can include the silyl protecting groups noted herein. In a further embodiment, for example and without limitation, the silyl group can optionally have one or more heteroatoms.

The term "acyl group" as used herein is not particularly limited, and should be known to a person of skill in the art. In one embodiment, for example and without limitation, the acyl group refers to the general formula "RC(=O)—", where R is a hydrocarbon; and can also include the acyl protecting groups noted herein.

The term "sulfonyl group" as used herein is not particularly limited, and should be known to a person of skill in the art. In one embodiment, for example and without limitation, the sulfonyl group refers to the general formula "RSO$_2$—", where R is a hydrocarbon. In a further embodiment, for example and without limitation, the sulfonyl group can optionally have one or more heteroatoms.

The term "alkoxycarbonyl group" as used herein is not particularly limited, and should be known to a person of skill in the art. In one embodiment, for example and without limitation, the alkoxycarbonyl group refers to the general formula "R—O—C(=O)—", where R is a hydrocarbon.

The term "alcohol protecting group" as used herein is not particularly limited, and should be known to a skilled worker or can be determined. In one embodiment, for example and without limitation, the protecting group forms an ester, ether or is a silyl-protecting group. In a further, embodiment for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS or TBS), tri-iso-propylsilyloxymethyl (TOM), or triisopropylsilyl (TIPS). In addition, the terms "protected geminal diol" and "protected vicinal dial" can have, for example and without limitation, two protecting groups for the hydroxyl groups, where the protecting groups can be as noted above. Alternatively, other diol protecting groups, such as, for example and without limitation, a ketal can also be used.

The term "hydrocarbon", as used herein, refers to a group that contains hydrogen and carbon, linked generally via a carbon backbone, but may optionally include heteroatoms. Thus, groups like methyl, ethoxyethyl, 2-pyridyl, and trifluoromethyl are considered to be hydrocarbyl for the purposes of this specification. Hydrocarbyl groups include, but are not limited to aryl, heteroaryl, carbocycle, heterocycle, alkyl, alkenyl, alkynyl, and combinations thereof.

The term "heteroatom", is not particularly limited and should be understood by a skilled worker. As used herein, the term means an atom of any element other than carbon or hydrogen. In one embodiment, for the example and without limitation, heteroatoms include nitrogen, oxygen, silicon and sulfur.

The term "alkyl" as used herein is not particularly limited and should be known to a person of skill in the art; and refers to substituted or unsubstituted saturated hydrocarbon groups, including straight-chain alkyl and branched-chain alkyl groups, including haloalkyl groups such as trifluoromethyl and 2,2,2-trifluoroethyl, etc. In one embodiment, for example and without limitation, the alkyl group is a $C_{1-6}$ alkyl.

The term $C_{1-6}$ alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-methylbutyl, 1,2-dimethylbutyl, 1-ethyl-2-methylpropyl, 1,1,2-trimethylpropyl, 1,1-dimethylbutyl, 2,2-dimethylbutyl, 2-ethylbutyl, 1,3-dimethylbutyl, 2-methylpentyl or 3-methyl pentyl.

The term "aryl" as used herein is not particularly limited, and should be known to a person of skill in the art. In one embodiment, for example and without limitation, the aryl group is a $C_{6-14}$ aryl. In another embodiment, for example and without limitation, aryl includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Examples of aryl include, for example and without limitation, benzene, toluene, naphthalene, phenanthrene, phenol, aniline, anthracene, and phenanthrene.

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is chloride, mesylate or tosylate. The functional groups that can be converted into leaving groups, in accordance with the specification, are not particularly limited. In one embodiment, for example the functional group can be a hydroxyl group that can be converted into a leaving group as described above.

The halide as used herein is not particularly limited and should be known to a person of skill in the art. In one embodiment, for example and without limitation, halides can include, Cl, Br or I. In a further embodiment, the halide is I.

In still another aspect, the specification relates to a process for preparation of halichondrin analogs, including for example, preparation of the compound of formula 3, or a pharmaceutically acceptable salt thereof. The process containing the step of performing an intramolecular cyclization reaction on a compound of formula 1b to form the compound of formula 3, where $R^1$, $R^2$, $R^3$, $R^4$, $R^5$, $R^{10}$, $R^{11}$, $R^{12}$, ----- and $R^{13}$ are as described herein.

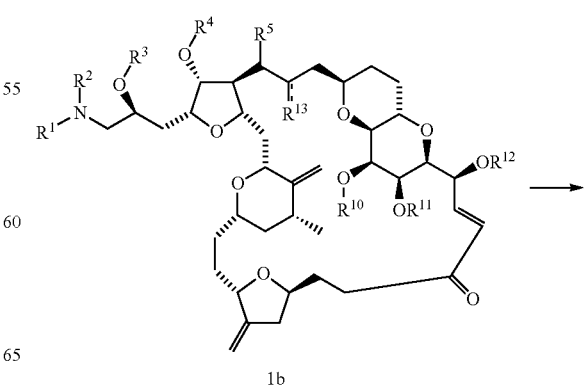

1b

-continued

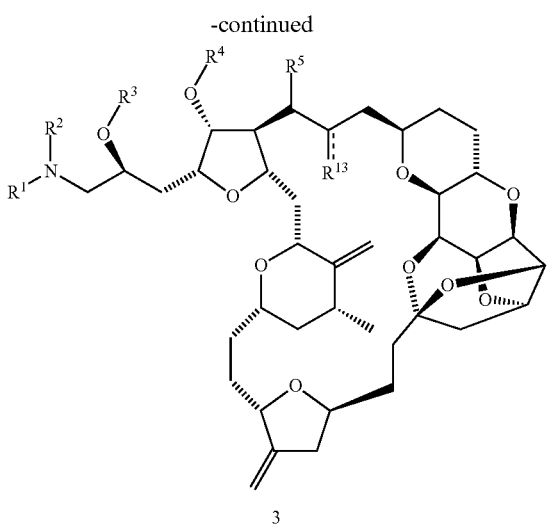

3

The method of performing the intramolecular cyclization reaction in accordance with the specification is not particularly limited. In one embodiment, for example and without limitation, $R^{10}$, $R^{11}$ and $R^{12}$ are H and the intramolecular cyclization reaction is performed using an acid. The type of acid used is also not particularly limited. In one embodiment, for example and without limitation, the acid is a mild acid that is also non-nucleophilic, and can be, for example but not limited to, pyridinium p-toluenesulfonate (PPTS), trialkyl ammonium sulfate and weak carboxylic acids, such as, for example and without limitation, acetic acid. Following the cyclization reaction, the reaction product can be treated with a base to neutralize the reaction mixture. The base used is not particularly limited. In one embodiment, the base is, for example, cesium carbonate ($Cs_2CO_3$). In addition, alkali metal based bases, such as an alkali metal carbonates, phosphates etc. can also be used.

In still another aspect, the specification relates to a process for preparation of the compound of formula 1, or a pharmaceutically acceptable salt thereof. The process containing the step of coupling a compound of formula 2b with a compound of formula 4 to form the compound of formula 1.

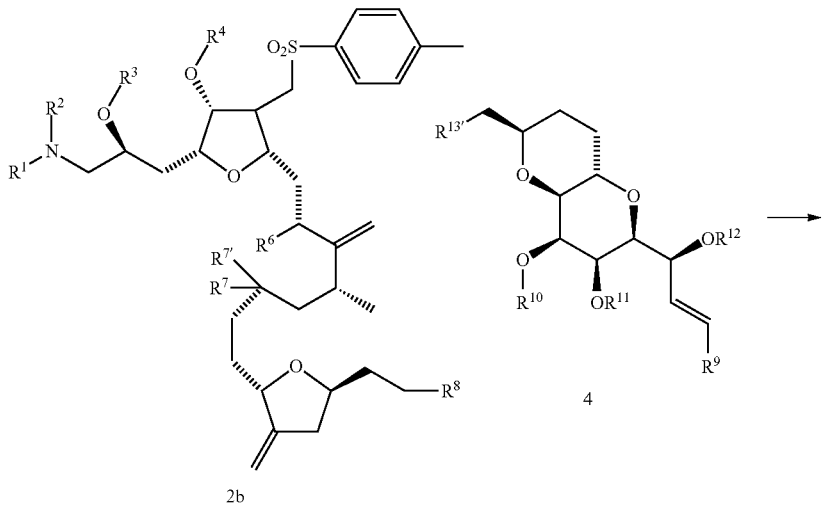

2b

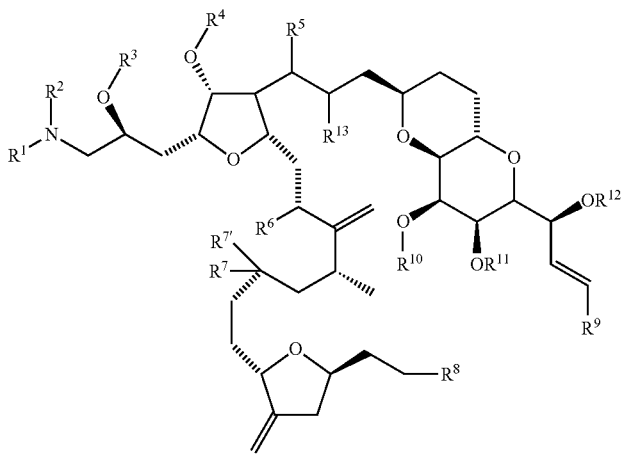

1 where $R^1$, $R^2$, $R^3$, $R^4$, $R^5$, $R^6$, $R^7$, $R^{7'}$, $R^8$, $R^9$, $R^{10}$, $R^{11}$, $R^{12}$, ----- and $R^{13}$ are as described herein; and $R^{13'}$ is —C(=O)$R^{22}$, wherein $R^{22}$ is H or $OR^{23}$, wherein $R^{23}$ is H or a hydrocarbon, the hydrocarbon optionally having one or more heteroatoms.

In one embodiment, for example and without limitation, the coupling reaction is performed by use of a base. The base used for the coupling reaction is not particularly limited, and can be determined by a skilled worker. In one embodiment, for example and without limitation, the base is lithium hexamethyldisilazide (LiHMDS), n-butyllithium (BuLi), lithium diisopropylamide (LDA), lithium diethylamide (LDEA), sodium amide (NaNH$_2$) or sodium hydride (NaH). In a further embodiment, the base used is n-butyllithium (BuLi).

In a still further aspect, the specification relates to a process for preparation of compound of formula 2, or a pharmaceutically acceptable salt thereof. The process involving coupling a compound of formula 5b with a compound of formula 6, to form the compound of formula 2.

example and without limitation, the coupling reaction performed is a Grignard reaction.

In still another aspect, the specification relates to a process for preparation of the compound of formula 5, or a salt thereof. The process containing the step of converting the terminal alcohol of the compound of formula 7 into an amine or substituted amine to form the compound of formula 5; where $R^1$, $R^2$, $R^3$ and $R^4$ are as described herein. One of $R^{5'}$ and $R^{5'''}$ is H and the other is —CH$_2$SO$_2$-(p-tolyl), or $R^{5'}$ and $R^{5'''}$ taken together form =CH—SO$_2$-(p-tolyl), wherein (p-tolyl) is p-tolyl is —(C$_6$H$_4$)—CH$_3$, with the —CH$_3$ at the para-position, as described herein. $R^{6'}$ is —CH$_2$—CH=CR$^{29}$R$^{29'}$, —CH$_2$—CH(OR$^{26}$)—CH(OR$^{26}$)R$^{29}$, —CH$_2$C(=O)—R$^{25}$ or —CH$_2$—CH$_2$—O—R$^{26}$, wherein $R^{29}$ and $R^{29'}$ each independently is H or a hydrocarbon, the hydrocarbon optionally having one or more heteroatoms; $R^{25}$ is H or $OR^{27}$, wherein $R^{27}$ is H or a hydrocarbon, the hydrocarbon optionally having one or more heteroatoms; and each $R^{26}$ independently is H or an alcohol protecting group.

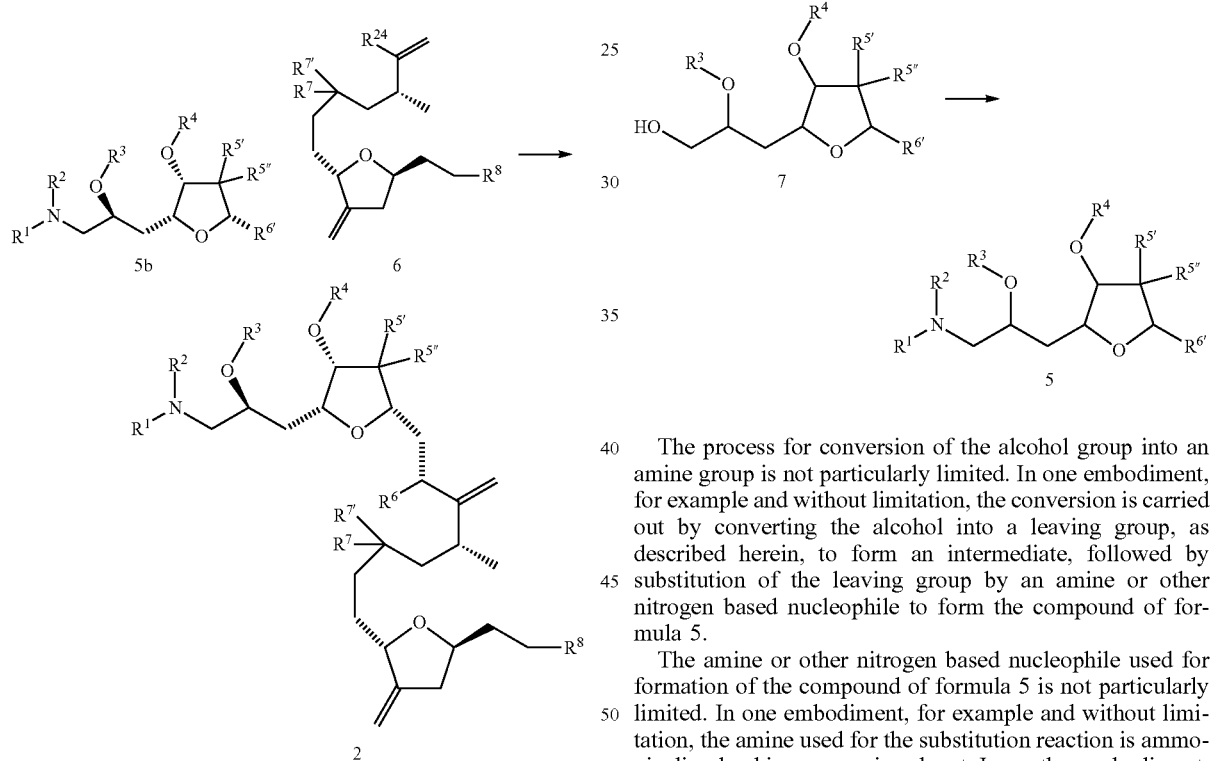

where $R^1$, $R^2$, $R^3$, $R^4$, $R^{5'}$, $R^{5'''}$, $R^6$, $R^7$, $R^{7'}$ and $R^8$ are as described herein; and $R^{6'}$ is —CH$_2$C(=O)R$^{25}$ or —CH$_2$CH$_2$OR$^{26}$; wherein $R^{25}$ is H or $OR^{27}$, wherein $R^{27}$ is H or a hydrocarbon, the hydrocarbon optionally having one or more heteroatoms, and $R^{26}$ is H or an alcohol protecting group. And, $R^{24}$ is a halide or a sulfonate.

The method of coupling the compound of formula 5b with the compound of formula 6 is not particularly limited. In one embodiment, for example and without limitation, where $R^{6'}$ is —CH$_2$C(=O)H, the coupling reaction is performed using a nickel/chromium catalyst, such as in the Nozaki-Hiyama-Kishi reaction. In a still further embodiment, for example and without limitation, the catalyst used for the coupling reaction is NiCl$_2$/CrCl$_2$. In another embodiment, for The process for conversion of the alcohol group into an amine group is not particularly limited. In one embodiment, for example and without limitation, the conversion is carried out by converting the alcohol into a leaving group, as described herein, to form an intermediate, followed by substitution of the leaving group by an amine or other nitrogen based nucleophile to form the compound of formula 5.

The amine or other nitrogen based nucleophile used for formation of the compound of formula 5 is not particularly limited. In one embodiment, for example and without limitation, the amine used for the substitution reaction is ammonia dissolved in an organic solvent. In another embodiment, for example and without limitation, the nitrogen based nucleophile is an azide. The azide used is also not particularly limited, and can be, in one embodiment for example, trimethylsilyl azide (TMSN$_3$).

In one embodiment, the compound formed after amination and where $R^3$ is H, the hydroxyl and amine functional groups of the compound are protected. Alcohol protecting group, as described above, can be used to protect the alcohol group, and where $R^3$ is as described above.

The amine protecting group as used herein is not particularly limited and should be known to a person of skill in the art. In one embodiment, for example and without limitation, amine protecting group can include carbobenzyloxy (Cbz), p-methoxybenzyloxy carbonyl (Moz), tert-butoxycarbonyl (t-BOC), 9-fluorenylmethoxycarbonyl (FMOC), acetyl (Ac), benzoyl (Bz), carbamate, p-methoxybenzyl (PMB), 3,4-Dimethoxybenzyl (DMPM) or p-methoxyphenyl (PMP). In a further embodiment, the amine protecting group is tert-butoxycarbonyl (t-BOC).

In one embodiment, for example, in the compound of formula 5, $R^{6'}$ is —$CH_2$—CH=$CH_2$. In another embodiment, for example, in the compound of formula 5 $R^{6'}$ is —$CH_2$—C(=O)H. The process for formation of the compound of formula 5 where $R^{6'}$ is —$CH_2$—C(=O)H is not particularly limited. In one embodiment, the compound of formula 5 where $R^{6'}$ is —$CH_2$—C(=O)H is formed from a compound where $R^{6'}$ is —$CH_2$—CH=$CH_2$. The process for conversion is not particularly limited. In one embodiment, for example and without limitation, the conversion is carried out by oxidatively cleaving the alkene to form the aldehyde.

The process for oxidatively cleaving the alkene to an aldehyde is not particularly limited and should be known to a person of skill in the art or can be determined. In one embodiment, for example and without limitation, the oxidative cleavage is performed using osmium tetroxide/sodium periodate or by ozonolysis.

In one embodiment in the compound of formula 5, one of $R^{5'}$ and $R^{5'''}$ is H and the other is —$CH_2SO_2$-(p-tolyl), or $R^{5'}$ and $R^{5'''}$ taken together form =CH—$SO_2$-(p-tolyl), where p-tolyl is —($C_6H_4$)—$CH_3$, with the —$CH_3$ at the para-position and $R^{28}$ is H or an alcohol protecting group. In a further embodiment, for example, the one of $R^{5'}$ and $R^{5'''}$ is —$CH_2SO_2$-(p-tolyl) and the carbon to which it is attached has the S-configuration. It has been found that the presence of the p-tolyl substituent in the structure of the intermediates disclosed herein, can affect the solubility profile of these compounds and their affinity to chromatographic stationary phase that can enhance resolution and efficiency of chromatographic purifications of these compounds, which can result in increased yields in the manufacturing process.

The process for formation of a compound of formula 5 where $R^{5'}$ and $R^{5'''}$, is as described herein, is not particularly limited. In one embodiment, for example a compound of formula 8 is converted into the compound of formula 5, where one of $R^{5'}$ and $R^{5'''}$ is —$CH_2SO_2$-(p-tolyl).

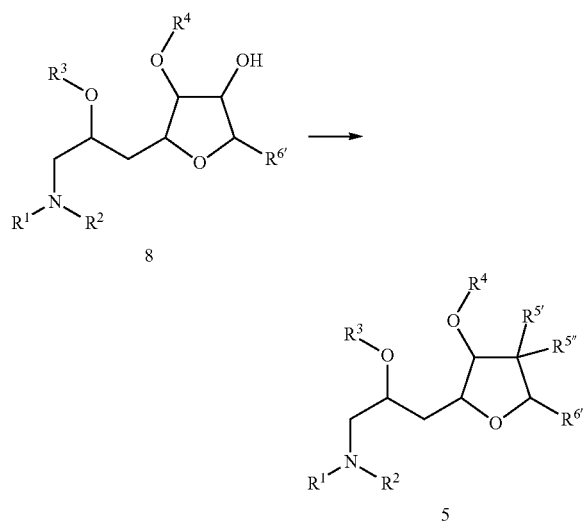

The process for conversion of the alcohol group into $R^{5'}$ and $R^{5'''}$, as described above, in the compound of formula 5 is not particularly limited. In one embodiment, for example and without limitation, the alcohol is oxidized to a ketone ("R'—C(=O)—R") prior to conversion to the compound of formula 5. The oxidation of the alcohol is not particularly limited, and should be known to a skilled worker or can be determined. In one embodiment, for example and without limitation, the oxidation is performed using a chromium-based reagent, such as Collins reagent, pyridinium dichromate (PDC) or pyridinium chlorochromate (PCC); activated dimethyl sulfoxide (DMSO), such as, Swern oxidation, Moffatt oxidation or Doering oxidation; or hypervalent iodine compounds, such as, Dess-Martin periodinane or 2-iodoxybenzoic acid.

Following oxidation of the alcohol to a ketone, the ketone functional group can be, in one embodiment, for example and without limitation, converted into an alkene. The reaction to convert a ketone to an alkene is not particularly limited, and should be known to a skilled worker or can be determined. In one embodiment, for example and without limitation, the ketone can be converted into an alkene using the Peterson olefination, the Wittig reaction or the like. In a further embodiment, for example and without limitation, the ketone is converted into an alkene using $(EtO)_2POCH_2SO_2$ (p-tolyl) or $(i-PrO)_2POCH_2SO_2$(p-tolyl).

Upon formation of the alkene, the compound can be reduced to alkane using a reducing agent. The reducing agent used in not particularly limited and can be determined by a skilled worker. In one embodiment, for example and without limitation, the reduction is carried out using a hydride source. The hydride source used is not particularly limited and should be known to a skilled worker or can be determined. In one embodiment, for example and without limitation, the hydride source is Stryker's Reagent ($[(PPh_3)CuH]_6$) or sodium borohydride triacetate ($NaBH(OAc)_3$).

In one embodiment in the compound of formula 5, $R^4$ is H, $C_{1-3}$ alkyl, $C_{1-3}$ haloalkyl or an alcohol protecting group, as described herein. In a further embodiment, for example and without limitation, $R^4$ is $C_{1-3}$ alkyl. In a still further embodiment, for example and without limitation, $R^4$ is methyl.

The description of the molecules disclosed herein has been made using abbreviations that should be known to a skilled worker or can be determined. Some of the abbreviations used include: p-tolyl is —($C_6H_4$)—$CH_3$, with the —$CH_3$ at the para-position, Ph for phenyl ($C_6H_5$—), Ar for aryl, which has been described herein, Ac for acetyl ($CH_3C$(=O)—), t-Bu for tert-butyl (($CH_3)_3C$—), $Et_3N$ for triethylamine (($CH_3CH_2)_3N$), CDI for 1,1'-carbonyldiimidazole $PPh_3$ for triphenylphosphine ((($C_6H_5)_3P$), Et for ethyl ($C_2H_5$—), $SO_2Ph$ for —$SO_2C_6H_5$, Me for methyl ($CH_3$—), MeO for methoxy ($CH_3O$), MeOH for methanol ($CH_3OH$), TBSO=OTBS=TBDMSO=OTBDMS for tert-butyldimethylsiloxy ((($CH_3)_3C)(CH_3)_2SiO$)—, $Boc_2O$ is for tert-butyl pyrocarbonate, $NaIO_4$ is for sodium periodate, $TMSN_3$ is for trimethylsilyl azide, Bn is for benzyl ($C_6H_5CH_2$—), TMSI is for trimethylsilyliodide ((($CH_3)_3SiI$), KHMDS is for potassium hexamethyldisilazide, TBAF is for tetra-butyl ammonium fluoride, mCPBA is for meta-chloroperoxybenzoic acid, DMAP is for dimethylaminopyridine, TsCl is for tosyl chloride, p-TSA is for para-toluylsulfonic acid, TMSOTf is for trimethylsilyloxy triflate, DCM for dichloromethane, THF for tetrahydrofurane, TBAC for tetrabutylammonium chloride and DMF is for dimethylformamide.

The process for preparation of compounds of formula 5 will now be described with reference to Schemes 1 and 2, shown below.

Scheme 1

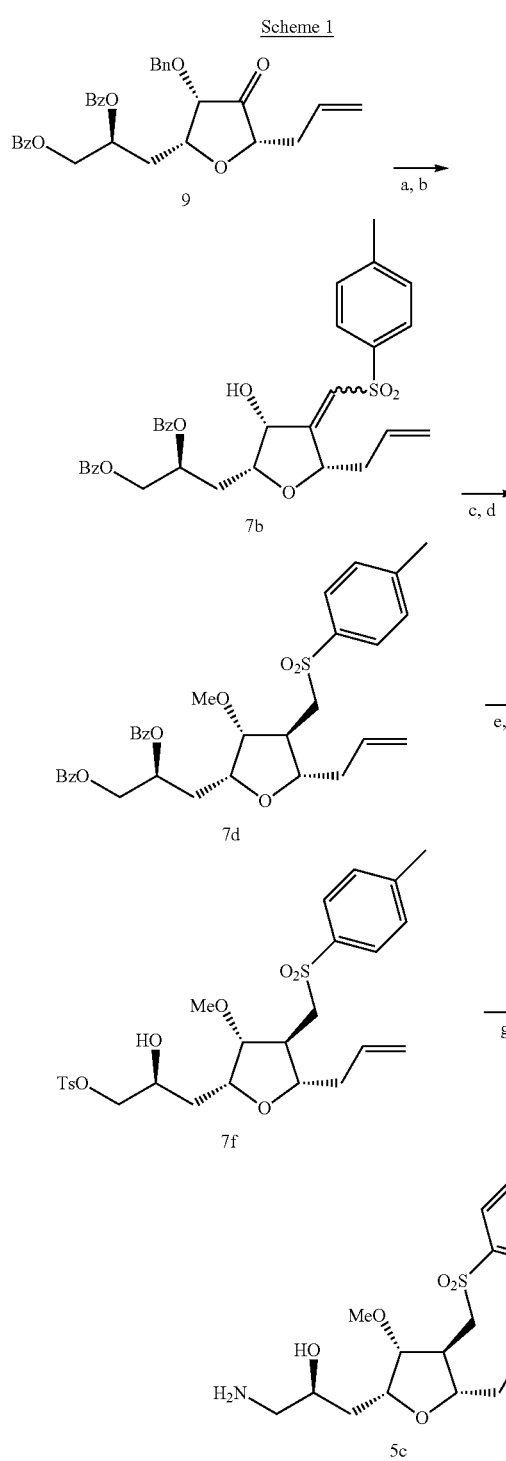

a) LiHMDS, dimethyl tosylmethylphosphonate (13), THF/toluene b) TMSI, DCM
c) NaBH(OAc)₃, TBAC, DME/toluene d) Me₃OBF₄, proton sponge, DCM e) K₂CO₃, MeOH f) TsCl, Bu₂SnO, NEt₃, DCM g) NH₃, MeOH The compound of formula 9 was prepared according to the procedures described in international patent application publication number WO 2005/118565, incorporated herein by reference. A Wittig or Horner-Wadsworth Emmons type reaction, affords unsaturated aryl sulfone 7a, as a mixture of Z:E geometrical isomers. The Z:E selectivity of the Horner-Wadsworth-Emmons reaction was found to be highly dependent on the nature of the O-alkyl group of the phosphonate coupling partner (13, Table 1). The ratio of Z:E increases significantly as the steric bulk of R increases from Me to i-Pr (entries 1-3). High ratios of the Z geometrical isomer was found to provide to provide benefits in later stages of the synthetic route (vide infra).

TABLE 1

Dependence on the structure of phosphonate 13 ((RO)₂P(O)CH₂SO₂Ar) towards the Z:E selectivity.

| entry | phosphonate | R    | Ar      | Z:E (14) |
|-------|-------------|------|---------|----------|
| 1     | 13a         | Me   | phenyl  | 5:1      |
| 2     | 13b         | Et   | phenyl  | 8:1      |
| 3     | 13c         | i-Pr | phenyl  | 19:1     |
| 4     | 13d         | Et   | p-tolyl | 7:1      |

The above reaction is followed by de-benzylation reaction using trimethylsilyl iodide (TMSI), which leads to the compound of formula 7b. The arylsulfonyl alkene can be reduced using a hydride source, for example and without limitation, NaBH(OAc)₃. As shown in scheme 1, the reduction of the double bond by NaBH(OAc)₃, with a vicinal free hydroxyl group can help to direct the reduction process and to obtain the desired stereoselectivity of the arylsulfonylmethyl moiety. It was found that the minor E geometrical isomer of 7a or 7b reacts significantly slower, or not at all, in the removal of the benzyl group and the selective reduction of the vinyl sulfone, thus increasing the desirability of high levels of Z selectivity in the synthesis. Therefore, in one embodiment, the specification discloses a process for preparation of intermediates having greater Z-selectivity and in a further embodiment, discloses a Z-isomer that can be useful in the preparation of the compounds disclosed herein.

The free hydroxyl is then methylated to form the compound of formula 7d. Removal of the benzoyl (Bz) protecting groups leads to a diol, the terminal alcohol in which can be converted into a leaving group, such as a tosylate (compound 7f), followed by nucleophillic substitution with an amine, such as ammonia, that leads to formation of the compound of formula 5c.

As shown in Scheme 2, reaction of the compound of formula 5c with di-tert-butyl pyrocarbonate (Boc₂O) and subsequent formation of an acetonide leads to the compound of formula 5e. The alkene in the compound of formula 5e can then be oxidized to an aldehyde of formula 5g, by oxidation using osmium tetroxide and N-methyl morpholine N-oxide, followed by reaction with sodium periodate (NaIO₄).

Scheme 2

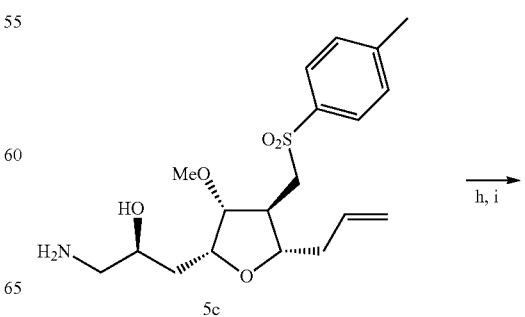

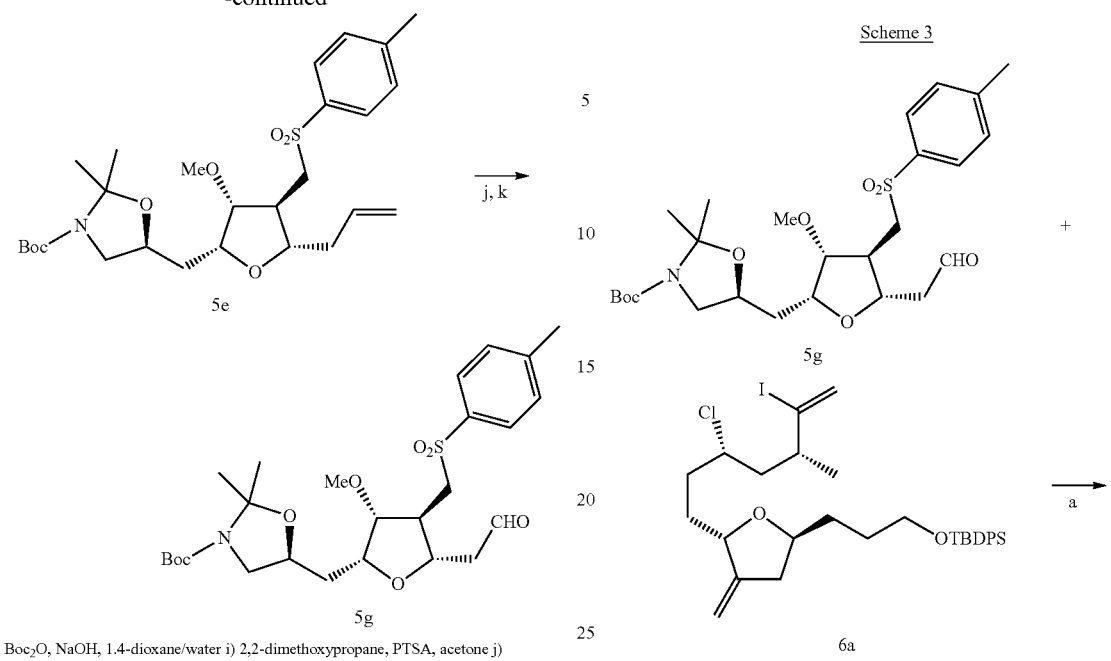

h) Boc₂O, NaOH, 1.4-dioxane/water i) 2,2-dimethoxypropane, PTSA, acetone j) OsO₄, NMO, t-BuOH/DCM k) NaIO₄, NaHCO₃, EtOAc/water The compound of formula 5, as disclosed herein, can be used for the preparation of compounds of formula 1, 2 or 3. In one embodiment, the synthesis of such compounds is disclosed in Schemes 3 and 4.

In Scheme 3, the compound of formula 5g is coupled to a compound of formula 6a to form the compound of formula 2c. Synthesis of the compounds, similar to the compound of formula 6a are described in PCT International Publication Number WO 2005/118565 A1, Guo, H. et al. J. Am. Chem. Soc., 2009, 131, 15387-93, Kim, D-S. et al. J. Am. Chem. Soc., 2009, 131, 15636-641, and Choi, H-w. et al. Org. Lett., 2002, v. 4 (25), 4435-38 (all incorporated herein by reference). In the embodiment shown, the coupling reaction is performed using a Ni/Cr catalyst, with the conditions for the coupling reaction being similar to those disclosed in U.S. Pat. No. 6,214,865 B1 or Kim, D-S. et al. J. Am. Chem. Soc., 2009, 131, 15636-641 (all incorporated herein by reference). Following coupling, displacement of the chloride can be achieved to form the tetrahydropyran ring. The reagent used is not particularly limited, and in the embodiment shown, the reagent is silver tetrafluoroborate (AgBF₄). The compound obtained can be desilylated using conditions that should be known to a skilled worker. In the embodiment disclosed, the desilylation is performed by tetra-butyl ammonium fluoride (TBAF), to obtain the compound of formula 2e. Coupling of the compound of formula 2e with the compound of formula 4a can be performed under basic conditions, similar to those as noted herein and disclosed in U.S. Pat. No. 6,214,865 B1 (incorporated herein by reference) to form an intermediate alcohol. Oxidation of the alcohol using reagents as noted-above results in formation of the compound of formula 1c. Oxidation of the alcohol followed by intra-molecular cyclization leads to the compound of formula 1e.

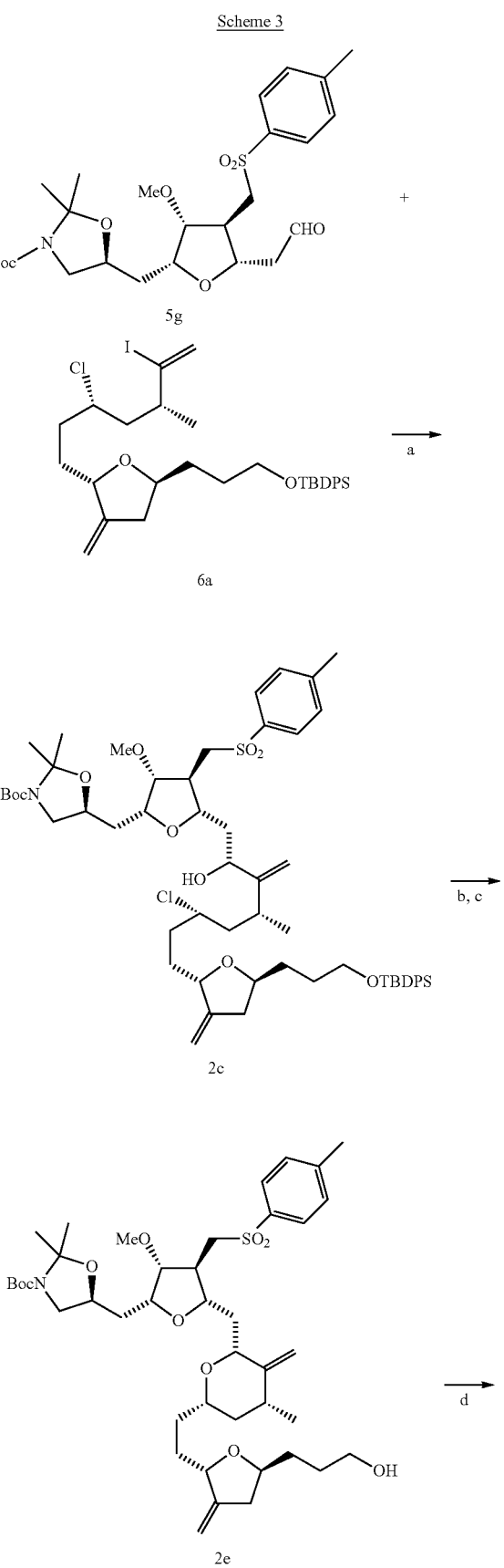

Scheme 3

-continued

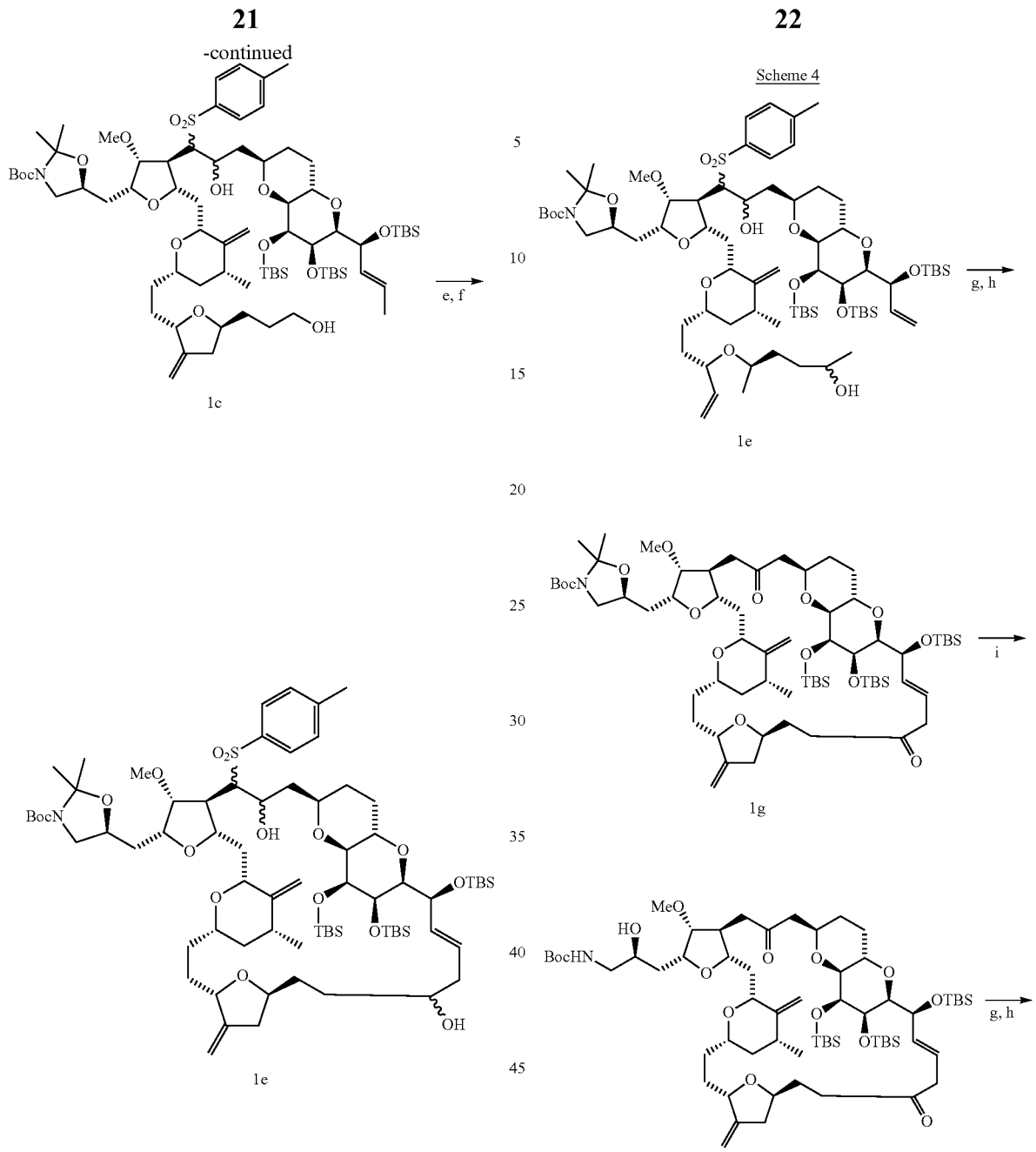

a) ligand (S)-2, NiCl$_2$ DMP, proton sponge, CrCl$_2$, LiCl, Mn, ZrCp$_2$Cl$_2$, MeCN b) AgBF$_4$, 2,6-di-t-butyl-4-methylpyridine, t-BuOAc c) TBAF, THF d) compound 3-14, n-BuLi, THF e) Dess-Martin, CH$_2$Cl$_2$ f) 4,4′-di-t-butyl-2,2′-bipyridyl, CrCl$_3$•3THF, NiCl$_2$•DMP, Mn, ZrCP$_2$Cl$_2$, THF As shown in Scheme 4, reduction of the arylsulfonyl moiety using a reducing agent, for example and without limitation, trivalent chromium and zinc, followed by subsequent oxidation using reagents as described above, can be performed to obtain compound of formula 1g. Removal of the isopropylidene protecting group can be carried out using an acid to form the compound of formula 1h. Removal of the silyl protecting group can be carried using a fluoride source, as should be known to a skilled worker, followed by intra-molecular cyclization using an acid leads to the compound of formula 1j. Removal of the Boc-protecting group using conditions that should be known to a skilled worker, leads to eribulin.

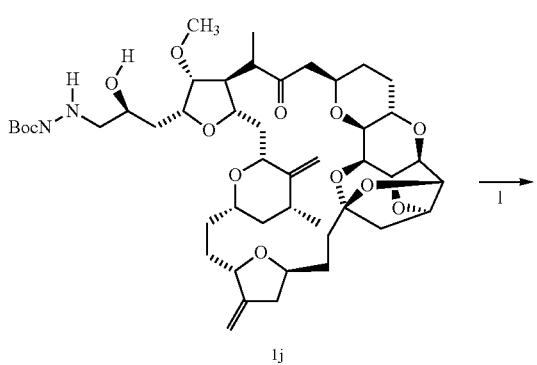

-continued

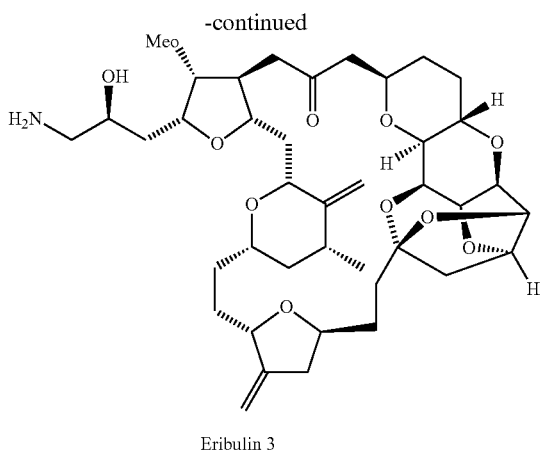

Eribulin 3 g) 4,4'-di-t-butyl-2,2'-bipyridyl, CrCl₃•3THF, Zn, THF h) Dess-Martin, CH₂Cl₂ i) pTSA, MeOH j) TBAF, AcOH, THF k) PPTS, CH₂Cl₂ l) TMSOTf, 2,6-lutidine, CH₂Cl₂

The formation of the salt of eribulin (3) or compounds of formula 1 and 2 are not particularly limited. The salt formed can be used for isolation and purification of the compound; and can lead to a product having higher purity and/or reduced amount of impurities. In one embodiment, for example and without limitation, the eribulin is reacted with an acid under conditions that should be known to a person of skill in the art or can be determined to form the desired salt. In a further embodiment, eribulin is reacted with methanesulfonic acid to form the eribulin mesylate salt.

The organic solvent used in the reactions described herein is not particularly limited and should be known to a person of skill in the art or can be determined. The particular solvent used would depend upon the reactants and the reaction being carried out, to allow the reaction to proceed.

Tubulin Polymerization Assays:

Biological activity of Halichondrin B, Eribulin, halichondrin B analogs and Eribulin analogs for example can be determined according to the methods described in Cancer Research, 2001, 61: 1031-1021 (incorporated herein by reference). In detail the polymerization of bovine brain tubulin in vitro can be assessed and compared with reference substances. The substance of interest can be dissolved in anhydrous DMSO and further diluted in 10% DMSO, 90% PEM buffer (PEM-buffer: 80 mM PIPES [Piperazine-N,N'-bis(2-ethanesulfonic acid)], pH 6.9, 1 mM EGTA (ethylene glycol tetraacetic acid), 1 mM magnesium chloride). Test samples can be prepared by combining in a total volume of 100 μl 3 mg/ml bovine brain tubulin (Cytoskeleton, Inc, Denver, Colo., USA), 1 mM ATP, 3% (volume/volume) glycerol, 1% DMSO in PEM-buffer. The polymerization reaction can be initiated by raising the temperature from 4° C. to 37° C. over a period of 3 minutes. Readout of the assay is the tubulin polymerization as determined for example by measuring the absorbance at 340 nm, measured over time for example once every minute for 60 minutes (Cancer Research, 61, page 1014, left row, paragraph 3 and FIG. 6 on page 1018).

A similar assay is described in Journal of Biological Chemistry, 1985, 26: 2819-2825 (incorporated herein by reference).

Cell Growth Inhibition Assays:

Cell growth inhibition assays are also described in Cancer Research, 2001, 61: 1031-1021 (incorporated herein by reference). Biological activity on viable human cancer cells for example can be shown by use of cell lines representing different types of human cancer, such as COLO 205 and DLD-1 (colon cancer), DU 145 and LNCaP (prostate cancer), HL-60 (promyelocytic leukemia), U937 (histiocytic lymphoma), MDA-MB-435 (human breast cancer), and LOX (human melanoma). These cells can be obtained from the American Type Culture Collection (ATCC), Rockville, Md., USA) or from the Division of Cancer Treatment-NCI Tumor Repository (Frederick, Md., USA) (LOX-cell line), or from Dr. Mary J. C. Hendrix, University of Iowa College of Medicine, Iowa City, Iowa, USA) (MDA-MB-435 cell line, MDA-MB-4355 available from ATCC). All cell lines can be grown at 37° C., 5% carbon dioxide at empirically optimized cell densities. All cell lines can be cultured under tissue culture conditions as recommended by ATCC. LOX cell line can be cultured in RPMI 1640 medium, 10% heat-inactivated fetal bovine serum, 2 mM L-glutamine, MDA-MB-435 cell line can be cultured in DMEM (high glucose), 10% heat-inactivated fetal bovine serum, 20 mM N-2-hydroxyethyl-piperazine-N'-2-ethanesulfonic acid, 1 mM sodium pyruvate.

For the biological cell growth inhibition assay, cells can be seeded in 96-well plates at 7,500 cells/well (except LNCaP, which can be seeded at 10,000 cells/well). All cells can be grown for 4 days in the presence of said substances of interest. Subsequently in order to quantitate cell numbers, sterile-filtered 3-(4,5-dimethylthiazol-2yl)-2,5-diphenyl tetrazolium bromide can be added to each well resulting in a final concentration of 0.5 mg/ml, incubation for 4 h at 37° C., addition of 150 μl 0.1 N HCl in isopropanol, gentle mixing and measurement of absorbance at 540 nm. Details of this method are described in Cancer Research, 61, 1031-1021, page 1013, last paragraph to page 1014 first paragraph, as well as in FIG. 2 and table 1 of the same publication. Furthermore this technique is described in Analytical Biochemistry, 1984, 139: 272-277, and in Journal of Immunological Methods, 1983, 65: 55-63 (all incorporated herein by reference).

For comparison reference substances such as the microtubule destabilizer vinblastine and the microtubule stabilizer paclitaxel can be used in in vitro tubulin polymerization or in cell growth inhibition tests.

Determination of Purity by HPLC:

Determination of the purity of Halichondrin B, Eribulin, Halichondrin B analogs and Eribulin analogs for example can be determined by High Pressure Liquid Chromatography (HPLC) as known in the art. The substance of interest is dissolved in a suitable solvent, for example in an organic solvent such as ethanol and subjected to HPLC. The elution profile of the substance of interest and of any potential impurities or degradation products is recorded. The percentage of purity of the substance of interest for example can then be calculated by determining the area below the peak of the substance of interest and separately the area below the peaks of all other substances eluted from the HPLC column. Alternatively the peak of the substance of interest and separately all other peaks can be collected, the HPLC-elution buffer be removed (for example by evaporation if the buffer is an organic solvent such as ethanol), thereby enabling weighing of the eluted substance of interest and the eluted other substances in order to calculate percentage of purity of the substance of interest.

EXAMPLES

The invention is now described by way of examples, which disclose embodiments of the inventions, and are not intended to be limiting of the invention as described and claimed herein.

Example 1

Preparation of Compound of Formula 7a

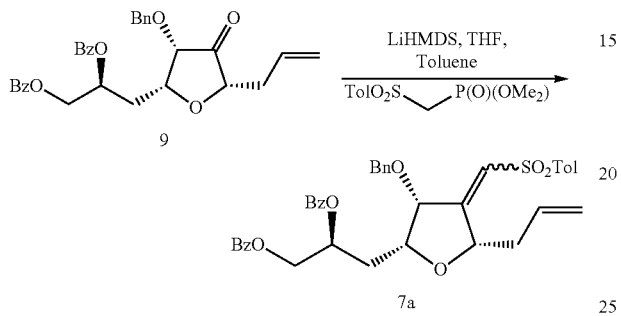

To a 4-5° C. solution of dimethyl tosylmethylphosphonate (17.6 g, 63.2 mmol, 1.3 eq) in tetrahydrofuran (75 mL) was added lithium bis(trimethylsilyl)amide solution (1M in THF, 58 mL, 1.3 eq) over 20 minutes. The mixture was stirred at 4-5° C. for 30 minutes and then warmed to room temperature. Additional tetrahydrofuran (50 mL) was added and the mixture was added to a solution of compound 9 (25.0 g, 48.6 mmol, 1 eq) in toluene (100 mL) over 1 hour at room temperature. The mixture was stirred for 1 h at room temperature and then cooled in an ice bath. The mixture was quenched with 0.5 M aq HCl (100 mL) and warmed to room temperature. The aqueous layer was extracted with toluene (50 mL). The combined organic layers were washed with water (100 mL), aqueous saturated NaHCO$_3$ (100 mL), and brine (100 mL). The organic layer was concentrated to dryness and purified by column chromatography using a gradient of ethyl acetate/heptane mixture (5%, 20%, 50%) as an eluent to give 27.5 g of 7a as an orange oil (85%) with alkene isomer ratio of 6:1.

Example 2

Preparation of Compound of Formula 7b

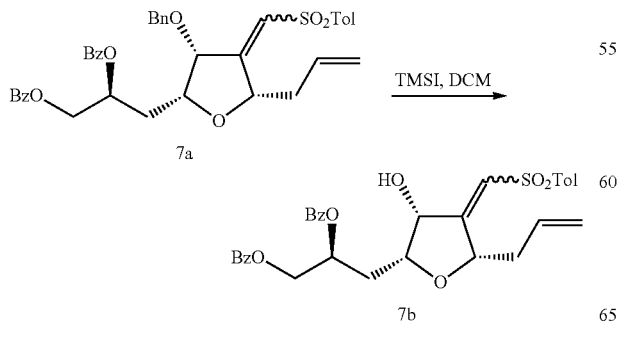

To a 4-5° C. solution of compound 7a (25.0 g, 37.4 mmol, 1 eq) in dichloromethane (250 mL) was added iodotrimethylsilane (10.7 mL, 75.0 mmol, 2 eq) over 15 minutes. The reaction was warmed to room temperature and stirred for 18 hours. The mixture was cooled to 4-5° C. and a solution of Na$_2$S$_2$O$_3$.H$_2$O (28 g) in aqueous saturated NaHCO$_3$ (175 mL) was added. The mixture was warmed to room temperature and water (50 mL) was added. The aqueous layer was extracted with dichloromethane (3×75 mL). The combined organic layers were washed with brine (50 mL) and concentrated to dryness. The resulting oil was purified by column chromatography using a gradient of ethyl acetate/heptane solutions (10%, 20%) as eluent to give 20.5 g of 7b as an orange oil (73%).

Example 3

Preparation of Compound of Formula 7c

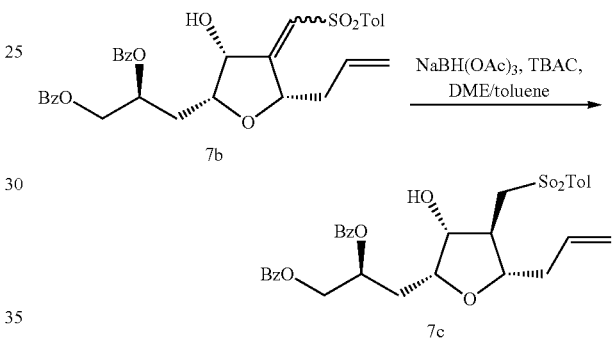

To a mixture of sodium triacetoxyborohydride (22.0 g, 104 mmol, 3 eq) in toluene (80 mL) and 1,2-dimethoxyethane (160 mL) was added tetrabutylammonium chloride (19.3 g, 69.4 mmol, 2 eq). The mixture was heated at 60° C. for 1 h. A solution of compound 7b (20.0 g) in toluene (80 mL) was added dropwise. The mixture was heated at 75° C. for 3 h. The mixture was cooled to room temperature and water (160 mL) was added. The organic layer was washed aqueous saturated NaHCO$_3$ (2×150 mL), and brine (150 mL). The organic layer was concentrated to dryness and the resulting oil was purified by column chromatography using a gradient of ethyl acetate/heptane mixture (25%, 50%) as an eluent to give 15.6 g of 7c as an orange oil (78%).

Example 4

Preparation of Compound of Formula 7d

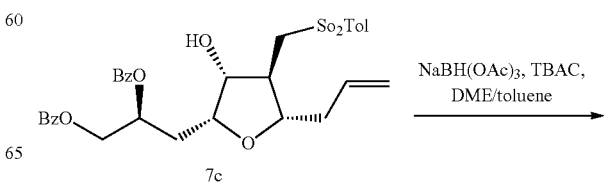

-continued

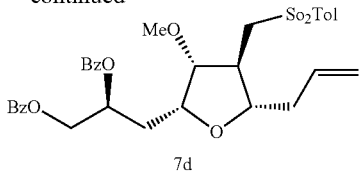

7d

To a solution of compound 7c (15.0 g, 25.9 mmol, 1 eq) in dichloromethane (150 mL) was added Proton-Sponge® (15.0 g, 70.0 mmol, 2.7 eq) and trimethyloxonium tetrafluoroborate (8.6 g, 64.8 mmol, 2.5 eq). The mixture was stirred at room temperature for 18 hours. The solids were filtered and washed with dichloromethane (20 mL). The filtrate was quenched with 1 M aqueous HCl (150 mL). The aqueous layer was extracted with dichloromethane (3×100 mL) and the combined organic layers were washed with brine (100 mL) and concentrated to dryness. The resulting oil was purified by column chromatography using a gradient of ethyl acetate/heptane mixture (30%, 50%) as an eluent to give 12.8 g of 7d as an orange oil (83%).

Example 5

Preparation of Compound of Formula 7f

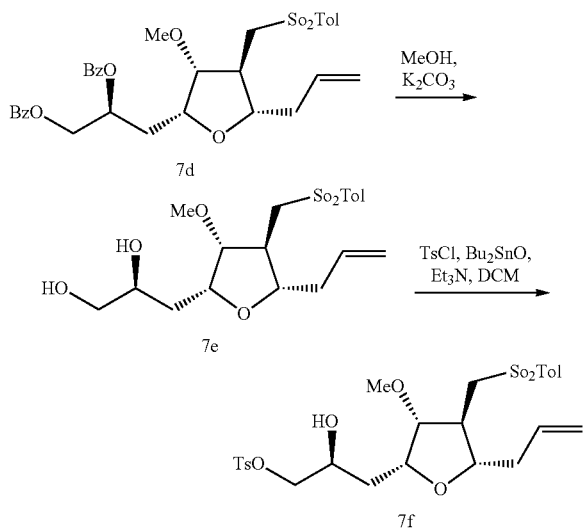

To a solution compound 7d (12.5 g, 21.1 mmol, 1 eq) in dichloromethane (15 mL) was added methanol (65 mL). The solution was cooled to 4-5° C. and potassium carbonate (2.9 g, 21.2 mmol, 1 eq) was added. The mixture was warmed to room temperature and stirred for 18 hours. The mixture was cooled to 4-5° C. and aqueous saturated NH$_4$Cl (40 mL) was added. The mixture was stirred for 30 minutes and ethyl acetate (100 mL) and water (100 mL) were added. The mixture was warmed to room temperature and the aqueous layer was extracted with ethyl acetate (3×50 mL). The combined organic layers were washed with brine (100 mL), dried with Na$_2$SO$_4$, and concentrated to dryness. The resulting compound 7e oil was carried forward to next step.

To a solution of compound 7e (based on 8 g of 7e) in dichloromethane (80 mL) was added dibutyltin(IV) oxide (0.10 g, 0.42 mmol, 0.02 eq), p-toluenesulfonyl chloride (3.9 g, 20.8 mmol, 1 eq), and triethylamine (2.9 mL, 20.8 mmol, 1 eq). The mixture was stirred at room temperature for 3 hours and water (40 mL) was added. The aqueous layer was extracted with dichloromethane (3×40 mL). The combined organic layers were washed with brine (20 mL), dried with Na$_2$SO$_4$, and concentrated to dryness. The resulting oil was purified by column chromatography using a gradient of ethyl acetate/heptane mixture (30%, 50%) as an eluent to give 9.5 g of 7f as an orange oil (85%).

Example 6

Preparation of Compound of Formula 5d

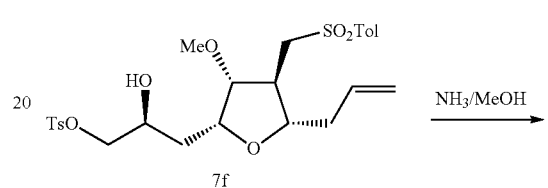

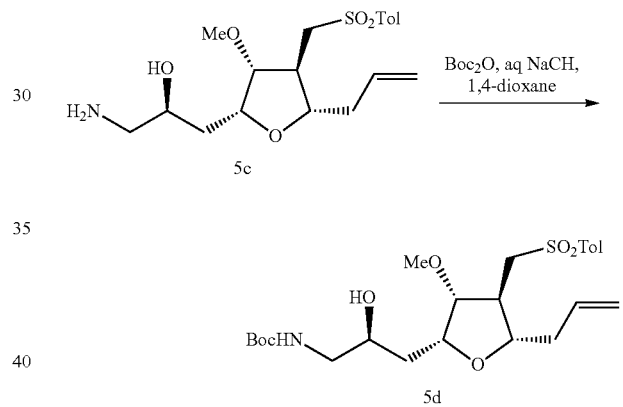

To compound 7f (9.0 g, 16.7 mmol, 1 eq) was added ammonia solution (7 M in methanol, 420 mL). The flask was capped and the reaction mixture was stirred at room temperature for 3 days. The reaction mixture was concentrated to dryness and dichloromethane (150 mL) and 2 N aqueous NaOH (50 mL) were added. The aqueous layer was extracted with dichloromethane (50 mL). The combined organics were washed with water (50 mL), brine (50 mL), dried with Na$_2$SO$_4$, and concentrated to dryness. The resulting compound 5c oil was carried forward to next step.

To a solution of compound 5c (based on 6.4 g of 5c) in 1,4-dioxane (80 mL) was added 1 N aqueous NaOH (80 mL). A solution of di-tert-butyl dicarbonate in 1,4-dioxane (80 mL) was added. The mixture was stirred at room temperature for 18 hours and then 1 M aqueous HCl was added to pH 6-7. The mixture was concentrated to half volume and ethyl acetate (200 mL) and water (200 mL) were added. The aqueous layer was extracted with ethyl acetate (2×200 mL). The combined organics were washed with brine and concentrated to dryness. The resulting oil was purified by column chromatography using a 70% ethyl acetate/heptane solution as eluent to give 6.5 g of 5d as an orange oil (80%).

Example 7

Preparation of Compound of Formula 5e

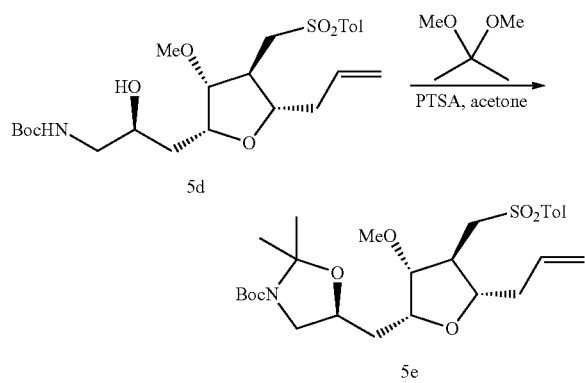

To a solution of 5d (6.5 g, 13.4 mmol, 1 eq) in acetone (130 mL) was added 2-dimethoxypropane (16.5 mL, 134.4 mmol, 10 eq) and p-toluenesulfonic acid monohydrate (0.26 g, 1.34 mmol, 0.10 eq). The mixture was stirred at room temperature for 18 h. Triethylamine (0.22 mL, 1.61 mmol, 0.12 eq) was added athe the reaction mixture was concentrated to dryness. The resulting oil was purified by column chromatography using a 40% ethyl acetate/heptane solution as eluent to give 6.0 g of 5e as a colourless oil (85%).

Example 8

Preparation of Compound of Formula 5g

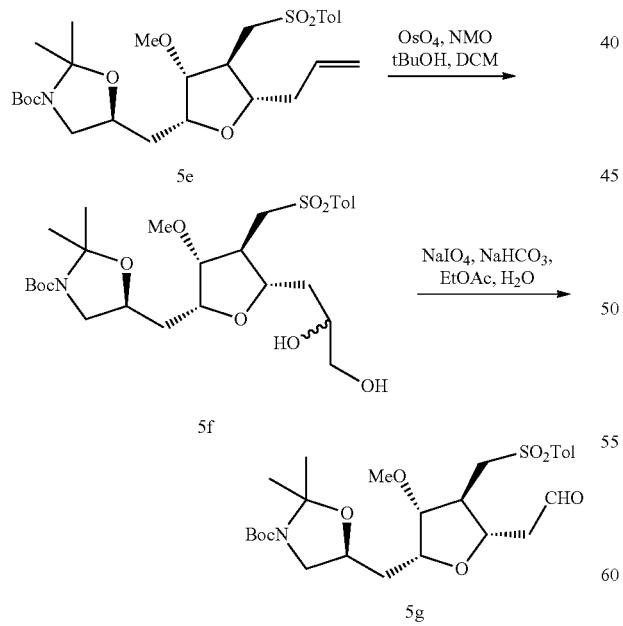

To a solution of (0.50 g, 0.95 mmol, 1 eq) and dichloromethane (5 mL) was added 4-methylmorpholine N-oxide (0.33 g, 2.86 mmol, 3 eq) and osmium tetroxide solution (2.5 wt % in tert-butanol, 0.12 mL, 0.01 mmol, 0.01 eq). The mixture was stirred at room temperature for 2.5 h. A 10% aqueous $Na_2S_2O_3$ solution was added and the mixture was stirred for 15 minutes. The aqueous layer was extracted with dichloromethane (2×3 mL). The combined organics were dried with $Na_2SO_4$ and concentrated to dryness. The resulting oil, compound 5f, was carried forward to next step.

To a 0° C. solution of compound 5f (based on 0.53 g of 5f) in ethyl acetate (4.5 mL) and water (4.5 mL) was added sodium periodate (0.30 g, 1.42 mmol, 1.5 eq). The mixture was stirred at 0° C. for 1 h. The solids were filtered and washed with ethyl acetate (6 mL). The filtrate was dried with $Na_2SO_4$ and concentrated to dryness. The resulting oil was purified by column chromatography using a 10% acetone/dichloromethane solution as eluent to give 0.38 g of 5g as a white foam (77%).

Example 9

Preparation of diethyl ((p-tolylthio)methyl)phosphonate

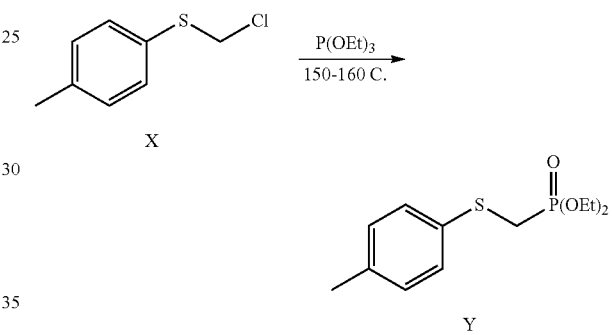

Chloromethyl 1-tolyl sulfide (19.2 g, 111.2 mmols, 1.0 eq) was added via a pressure-equalizing dropping funnel to a pre-heated solution of triethyl phosphite (45 mL, 260 mmols, 2.4 eq) at 130 to 150° C. The addition was commenced at 130° C. and during the course of the addition the internal temperature was increased to 150° C. The addition was complete after 35 min and the reaction mixture was maintained at 150 to 160° C. for 20 hrs. The reaction mixture was cooled to 50-60° C. and the excess triethyl phosphite was removed under reduced pressure (3-4 mbar at 50-60° C.) to yield crude Y. The crude product was purified by passing through a plug of silica gel (250 g) using a gradient of methyl tert-butyl ether (MTBE)/heptanes mixture (0:1, 1:1, 1:0) as an eluent to afford Y (28.8 g, 105.0 mmols, 94.4%) as a colourless liquid.

Example 10

Preparation of diethyl (tosylmethyl)phosphonate

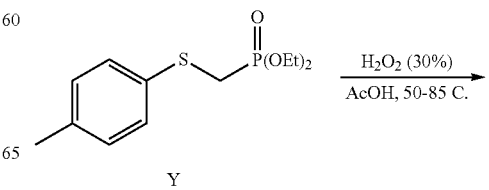

-continued

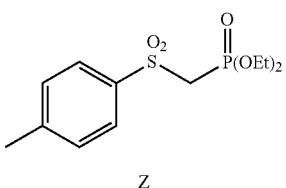

Z

H$_2$O$_2$ (30%, 30 mL, 290 mmols, 2.9 eq) was added via a pressure-equalizing dropping funnel to a solution of sulfide Y (27.5 g, 100 mmols, 1.0 eq) in glacial HOAc (100 mL) heated to 50° C. over 45 min. The reaction mixture was then heated to 85° C. for 3.5 hrs. The reaction mixture was then poured into cold aqueous NaOH (100 mL 50% wt NaOH mixed with 500 mL crushed ice) over 15 min keeping the temperature 25° C. The product was extracted into DCM (5×) and the combined organic layers were washed with saturated NaHSO$_3$ (3×) until all of the excess oxidant was consumed. The organic layer was dried over MgSO$_4$, filtered, and then evaporated to dryness under reduced pressure to yield crude Z (38 g). The crude product was purified by silica gel chromatography (Biotage, 340 g KP-Sil cartridge) using a gradient of methyl tert-butyl ether (MTBE)/heptanes mixture (1:1, 1:0) as an eluent to afford pure Z (22.2 g, 72.5 mmols, 72.5%) as a white solid.

Example 11

Preparation of Compound of Formula 2c

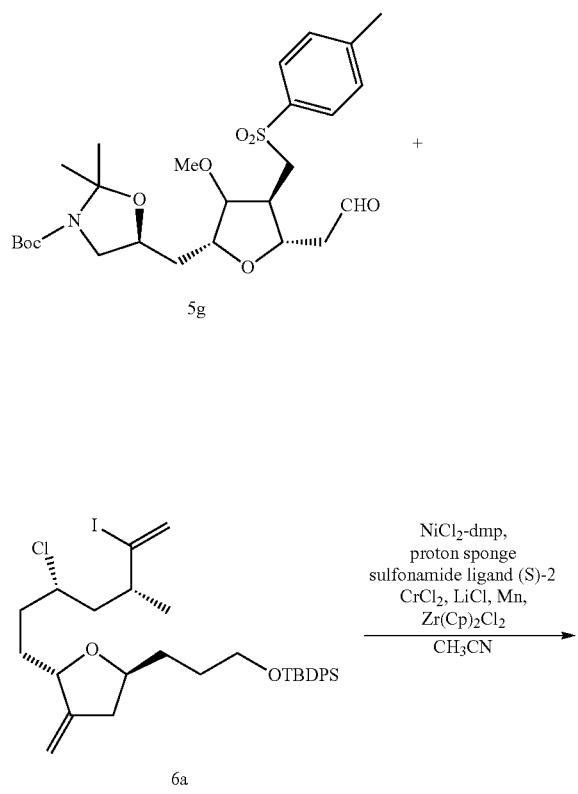

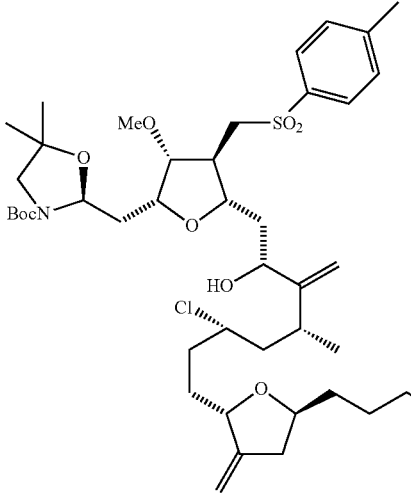
2c

(S)-2 =

All reagents and solvents are stored in a glovebox. Substrates 5g and 6a are azeotropically dried 2× with toluene, before introduction into the glovebox. A 100 mL round-bottom flask equipped with a stir bar was oven dried and cooled under inert atmosphere during introduction to the glovebox.

To a 100 mL round-bottom flask equipped with a stir bar, under inert atmosphere, were added CrCl$_2$ (691 mg, 5.62 mmol, 1.0 eq), sulfonamide ligand (S)-2 (1.93 g, 6.18 mmol, 1.1 eq) and proton sponge (1.33 g, 6.18 mmol, 1.1 eq). The solid reagents were suspended in acetonitrile (25 mL), producing a dark blue-green solution, which was stirred vigorously at room temperature for 1 hour. To the dark blue-green solution, lithium chloride (477 mg, 11.24 mmol, 2.0 eq), manganese (618 mg, 11.24 mmol, 2.0 eq), Zr(Cp)2Cl2 (1.87 g, 6.18 mmol, 1.1 eq) and NiCl$_2$.dmp (38 mg, 0.11 mmol, 0.02 eq) were added, followed by a suspension of 6a (3.66 g, 5.62 mmol, 1.0 eq) and 5g (3.28 g, 6.24 mmol, 1.1 eq) in acetonitrile (25 mL). The reaction vessel was capped and stirred vigorously for 16 hours. Another portion of lithium chloride (477 mg, 11.24 mmol, 2.0 eq) and NiCl$_2$.dmp (38 mg, 0.11 mmol, 0.02 eq) were added and the reaction was left stirring at room temperature for 4 hours more. The reaction mixture was then poured into a suspension of Florisil® (<200 mesh, 90 g) in methy tert-butyl ether (MTBE) (300 mL) and stirred at rt for 1 hour. The mixture was filtered over silica gel and rinsed with MTBE and several times with 8/2 dichloromethane/acetone. The filtrate was concentrated and subsequently purified by column chromatography using a Biotage Isolera, 100 g Snap column and 5-10% acetone in dichloromethane as eluent. The product 2c was afforded as a white foam (4.27 g, 72%) and used as is.

Example 12

Preparation of Compound of Formula 2d

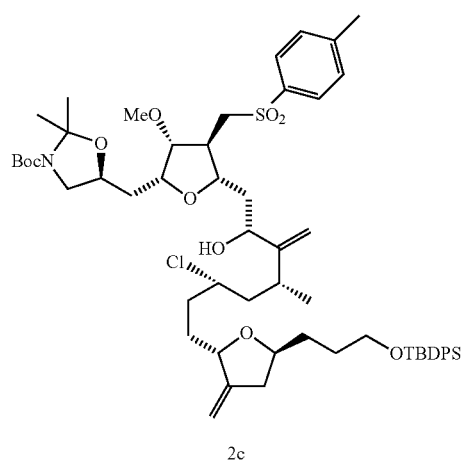

2c

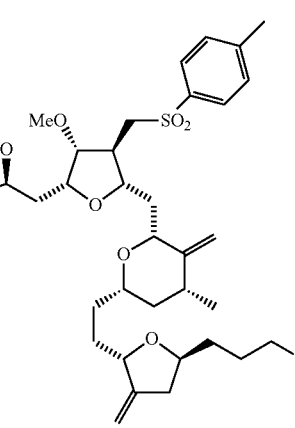

2d

Compound 2c (4.38 g, 4.17 mmol, 1.0 eq.) was dissolved in tBuOAc (220 mL) and the resulting solution was cooled to 0° C., under N₂. 2,6-Di-tert-butyl-4-methylpyridine (4.28 g, 20.85 mmol, 5.0 eq) was added, followed by silver tetrafluoroborate (2.43 mg, 12.51 mmol, 3.0 eq). The reaction flask was immediately removed from the cold bath, wrapped in aluminum foil and left stirring at room temperature for 16 hours. The reaction was quenched with saturated aqueous ammonium chloride solution (150 mL). The resulting mixture was extracted with MTBE (3×100 mL), dried over MgSO₄, filtered and concentrated to afford a colourless oil. The crude product was purified by column chromatography using Biotage Isolera, 100 g Snap Ultra column and 0-10% acetone in dichloromethane to afford the product 2d as a white foam (3.1 g, 74%).

Example 13

Preparation of Compound of Formula 2e

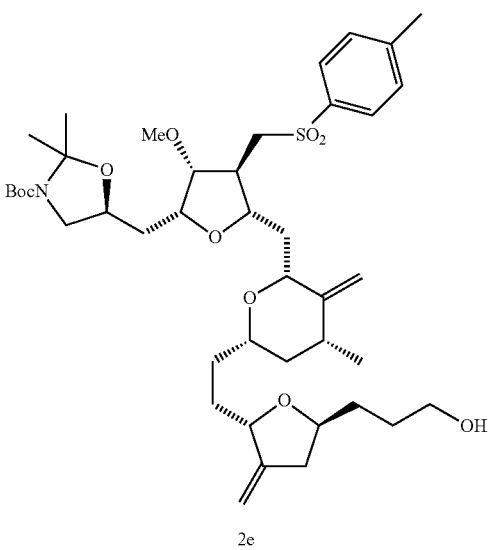

2e

Compound 2d (3.1 g, 3.1 mmol, 1.0 eq) was dissolved in anhydrous THF (31 mL), at room temperature, under N₂. Tetrabutylammonium fluoride (1M in THF, 4.0 mL, 4.0 mmol, 1.3 eq) was added in one portion and the reaction mixture was stirred at room temperature for 16 hours. The reaction was quenched with saturated aqueous ammonium chloride solution (50 mL) and the mixture was extracted with MTBE (3×50 mL). The combined organic layers were dried over MgSO₄, filtered and concentrated. The crude product was purified by column chromatography using a Biotage Isolera, 100 g Snap Ultra column and 10-30% acetone in dichloromethane as an eluent. The product 2e was afforded as a white foam (2.0 g, 84%), which upon drying could be handled like a solid.

Example 14

Preparation of Compound of Formula 1c

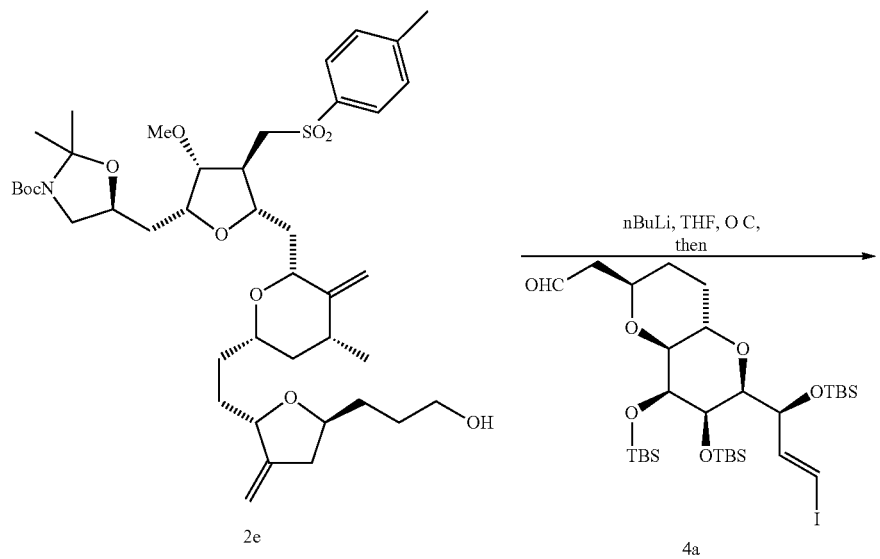

Compound 2e (991 mg, 1.28 mmol, 1.0 eq.) was dissolved in THF (13 mL) and the solution was cooled to 0° C. nBuLi (1.4M in hexane) was added dropwise until the bright yellow colour of the sulfone anion was just visible and persisted (1.12 mL) and a second aliquot of nBuLi (0.91 mL, 1.28 mmol, 1.0 eq) was then added to the reaction mixture. The resulting yellow solution was stirred at 0° C. for 10 min and then cooled to −70° C. Compound 4a (1.42 g, 1.92 mmol, 1.5 eq) was dissolved in hexanes (20 mL) and added to the reaction mixture, which was stirred at −70° C. for an additional 45 min. The cooling bath was removed and reaction was quenched with the addition of saturated aqueous ammonium chloride solution (20 mL) and the resulting mixture was extracted with MTBE (3×20 mL). The combined organic layers were washed with brine (20 mL), dried over MgSO$_4$, filtered and concentrated. The crude material was purified by column chromatography using a Biotage Isolera, 100 g Snap column and 5-20% acetone in dichloromethane as an eluent. 1c was obtained as a white foam (1.36 g, 70%).

Example 15

Preparation of Compound of Formula 1d

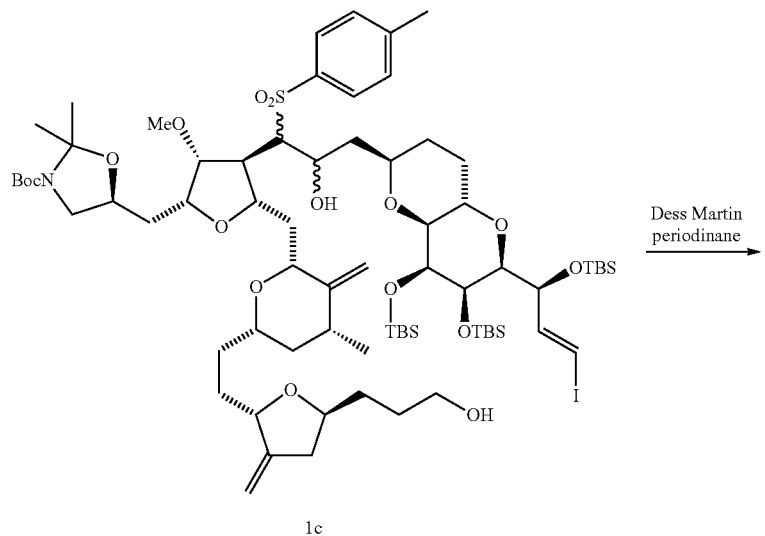

1c

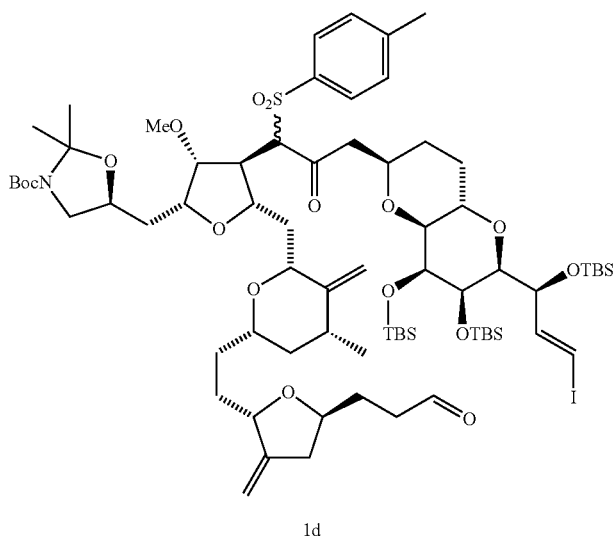

1d

Compound is (2.38 g, 1.57 mmol, 1.0 eq.) was dissolved in dichloromethane (16 mL) at room temperature. Dess Martin periodinane (1.66 g, 3.92 mmol, 2.5 q) was added in one portion and the reaction mixture was stirred for 1.5 hours. The reaction was quenched by the addition of saturated aqueous sodium bicarbonate solution (75 mL) and 10% (w/w) sodium thiosulfate solution (75 mL) and further diluted with MTBE (50 mL) The resulting mixture was stirred for 60 min, diluted with brine (15 mL) and the layers were separated. The aqueous phase was further extracted with MTBE (2×30 mL) and the combined organic layers were dried over MgSO$_4$, filtered and concentrated. The crude product was purified by column chromatography using a Biotage Isolera, 100 g Snap Ultra column and 5-10% acetone in dichloromethane as an eluent. The product 1d was afforded as a white foam (1.71 g, 72%).

Example 16

Preparation of Compounds of Formula 1e/1f

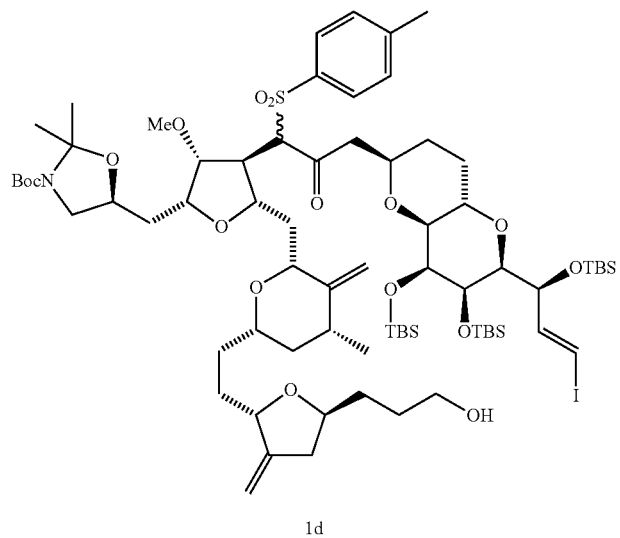

1d

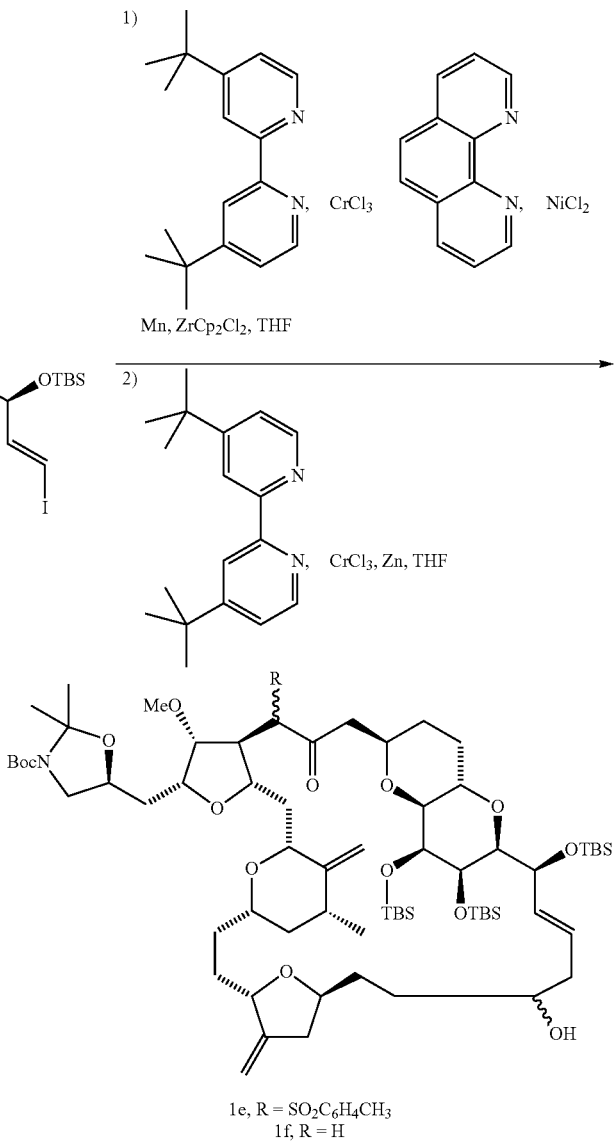

1e, R = SO$_2$C$_6$H$_4$CH$_3$
1f, R = H

All reagents are stored in a glovebox. A 50 mL round-bottom flask equipped with a stir bar was oven dried and cooled under inert atmosphere during introduction to the glovebox.

To a 50 mL round-bottom flask equipped with a stir bar, under inert atmosphere, were added CrCl$_3$.3THF (61 mg, 0.16 mmol, 1.0 eq), 4,4'-tert-butyl-2,2'-bipyridyl (44 mg, 0.16 mmol, 1.0 eq), NiCl$_2$.dmp (11 mg, 0.03 mmol, 0.2 eq), manganese (36 mg, 0.65 mmol, 4.0 eq) and Zr(Cp)$_2$Cl$_2$ (71 mg, 0.24 mmol, 1.5 eq). The reaction vessel was sealed with a rubber septum and brought outside the glovebox. Anhydrous THF (6 mL) was added to the round bottom flask and the resulting mixture was stirred at room temperature for 30 minutes.

Compound 1d (244 mg, 0.16 mmol, 1.0 eq.) was dissolved in anhydrous THF (6 mL) and added to the reaction mixture dropwise at room temperature and allowed to stir for 16 hours. The reaction mixture was then poured into a slurry of florisil (5 g) in MTBE (50 mL) and stirred for 30 minutes. The mixture was filtered over celite, rinsed with MTBE followed by 8/2 dichloromethane/acetone (40 mL) and concentrated to afford a mixture of the products 1e/1f (~1:3) as a brown oil.

A 50 mL round-bottom flask was charged with 1e/1f mixture (0.16 mmol, 1.0 eq), equipped with a stir bar and introduced into a glovebox. To the reaction vessel were added CrCl$_3$.3THF (362 mg, 0.96 mmol, 6.0 eq), 4,4'-tert-butyl-2,2'-bipyridyl (389 mg, 1.45 mmol, 9.0 eq) and Zn (318 mg, 4.83 mmol, 30.0 eq). The round-bottom flask was sealed with a rubber septum and brought outside the glovebox. Anhydrous THF (12 mL) was added to the reaction mixture and stirred at room temperature for 16 hours. The solvent was then removed under reduced pressure. The residue was suspended in dichloromethane, filtered over silica gel with 5-20% acetone in dichloromethane as an eluent to afford the product as a green foam (190 mg) which was carried on to the next step as is.

Example 17

Preparation of Compound of Formula 1g

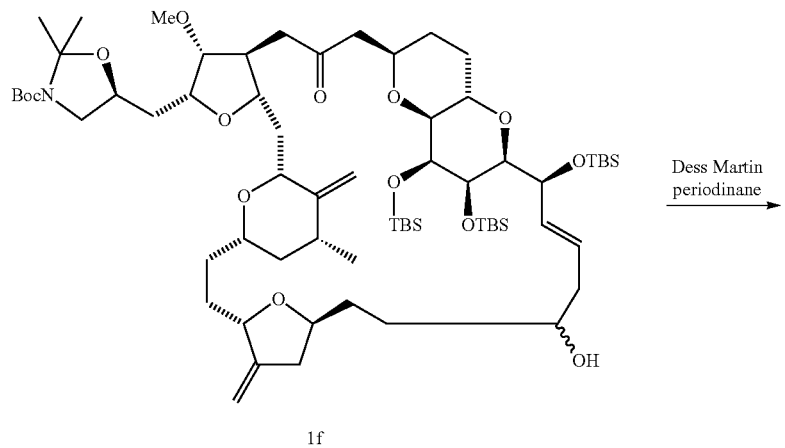

1f

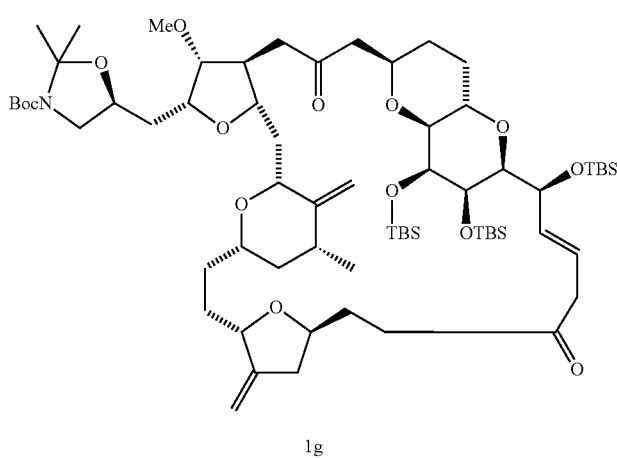

1g

Compound 1f (190 mg, 0.15 mmol, 1.0 eq.) was dissolved in dichloromethane (2 mL) at room temperature. Dess Martin periodinane (98 mg, 0.23 mmol, 1.5 eq) was added in one portion and the reaction mixture was stirred for 1.5 hours. The reaction mixture was quenched with saturated aqueous sodium bicarbonate solution (3 mL) and 10% $Na_2S_3O_3$ solution (3 mL), diluted with MTBE (10 mL) and stirred at room temperature for 1.5 hours. The mixture was diluted with brine (5 mL) and the layers separated. The aqueous phase was extracted twice more with MTBE (5 mL each) and the combined organics were dried over $MgSO_4$, filtered and concentrated. The crude product was purified by column chromatography using a Biotage Isolera, 50 g Snap column pre-packed with silica gel using 5-10% acetone in dichloromethane as an eluent. Product 1g was afforded as a white foam (101 mg, 51% over 3 steps).

Example 18

Preparation of Compound of Formula 1h

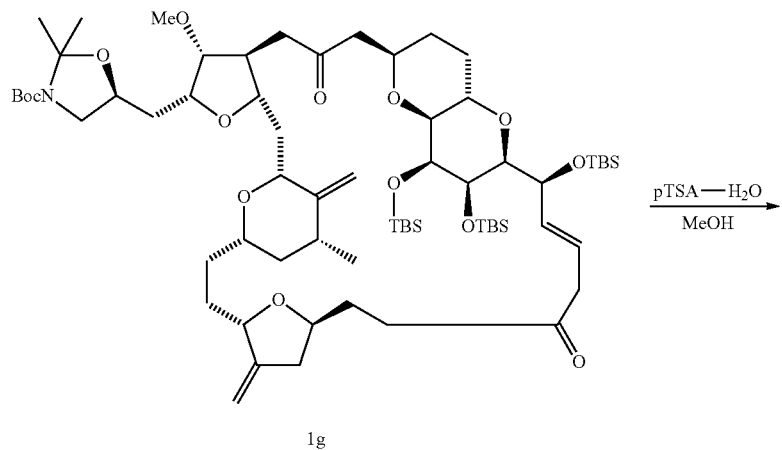

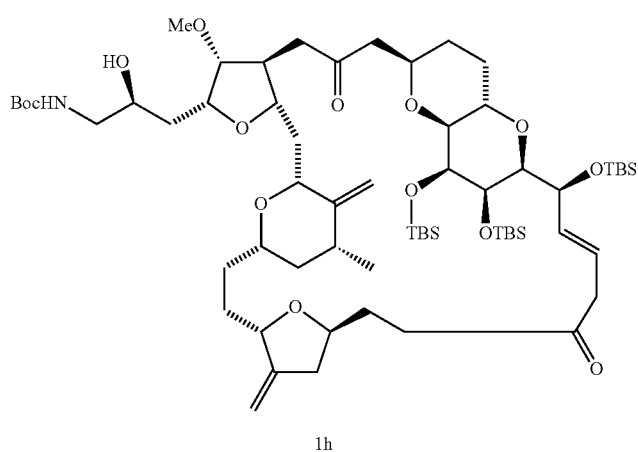

Compound 1g (415 mg, 340 μmol, 1.0 eq) was dissolved in MeOH (7 mL). p Toluenesulfonic acid monohydrate (13 mg, 68 μmol, 0.2 eq) was added in one portion at room temperature and the reaction was stirred at room temperature for 4 hours. The reaction mixture was diluted with dichloromethane and quenched with sat. aq. sodium bicarbonate solution (10 mL). The layers were separated and the aqueous phase was extracted twice more with dichlormethane (2×15 mL). The combined organic layers were washed with water (15 mL), brine (15 mL), dried over $MgSO_4$, filtered and concentrated to afford a crude 1h that was carried on to the next step as is.

Example 19

Preparation of Compound of Formula 1j

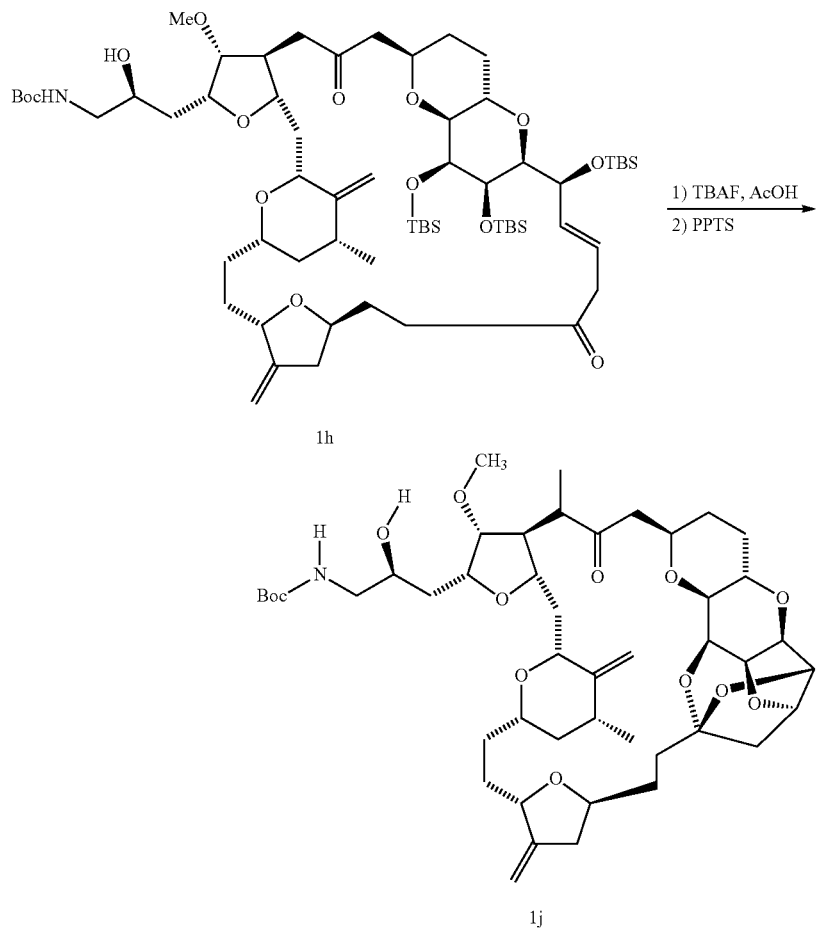

Compound 1h (340 μmol, 1.0 eq) was dissolved in anhydrous THF (10 mL) at room temperature, under N$_2$. Acetic acid (58 μL, 1.02 mmol, 3.0 eq) was added, followed by a solution of TBAF (1M in THF, 2.0 mL, 2 mmol, 6 eq). The reaction mixture was stirred for 20 hours. Calcium carbonate (408 mg, 4.08 mmol, 12.0 eq) and Dowex 50WX8-400 resin (1.23 g) were added to the reaction mixture and stirring was continued for 1 hour. The reaction mixture was diluted with ethyl acetate and filtered over celite. The solvent was removed under reduced pressure and the residue was dissolved in dichloromethane and filtered over a plug of silica gel using 1/1 dichloromethane/acetone. The solvent was removed under reduced pressure and the residue was dissolved in anhydrous dichloromethane (15 mL). PPTS (427 mg, 1.7 mmol, 5.0 eq) was added and the reaction mixture was stirred at room temperature for 1.5 hours. Half of the reaction mixture was applied directly to a 25 g Snap column for chromatography using a Biotage Isolera and 30-60% MTBE in dichloromethane as an eluent. The product 1j was afforded as a colourless oil (85 mg, 60%, 3 steps).

Example 20

Preparation of Eribulin

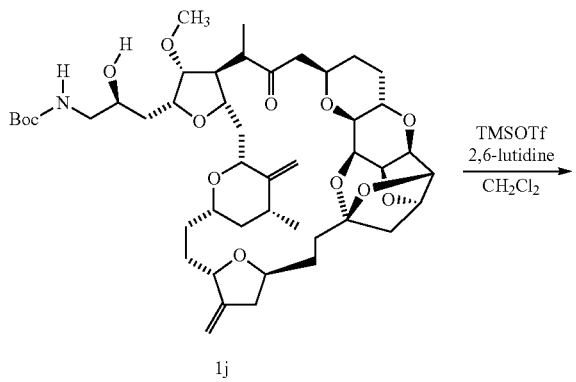

47

-continued

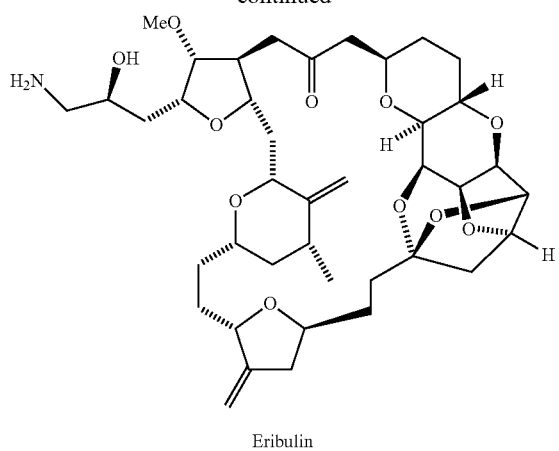

Eribulin

Compound 1j (133 mg, 160 µmol, 1.0 eq) was dissolved in anhydrous dichloromethane (20 mL) and cooled to 0° C. To this solution was sequentially added 2,6-lutidine (0.09 mL, 0.8 mmol, 5.0 eq), and TMSOTf (0.12 mL, 0.64 mmol, 4.0 eq) and the cooling bath was removed. The reaction was stirred at room temperature for 1.5 hours and another portion of 2,6-lutidine (5.0 eq) and TMSOTf (4.0 eq) were added at room temperature. The reaction was further stirred for 1 hour and quenched with water (10 mL). The layers were separated and the organic phase was washed with additional water (2×10 mL), brine (10 mL), dried over $MgSO_4$ and concentrated under reduced pressure. The residue was dissolved in MeOH (10 mL), a catalytic amount of $K_2CO_3$ was added at room temperature and the resulting mixture was stirred for 2 hours. The reaction was diluted with dichloromethane and quenched with water (10 mL). The layers were separated and the aqueous phase was further extracted with dichloromethane (5×10 mL) The combined organic layers were washed with brine (20 mL), dried over $MgSO_4$, filtered and concentrated. The residue was dissolved in dichloromethane and purified by column chromatography on silica gel, using 1:9 $MeOH:CH_2Cl_2$ to 1:9:90 $NH_4OH$:$MeOH:CH_2Cl_2$ as eluent. The product was afforded as a white amorphous solid (103 mg, 88%).

Example 21

Preparation of Eribulin Mesylate

Eribulin mesylate (3) was prepared from Eribulin according to the conditions described in US patent application publication number US 2011/0184190, incorporated herein by reference.

Example 22

Preparation of Compound of Formula 9

The compound of formula 9 was prepared according to the procedures described in international patent application publication number WO 2005/118565, incorporated herein by reference.

48

Example 23

Preparation of Compound of Formula 4a

The compound of formula 3-14 was prepared according to the procedures described in international patent application publication number WO 2005/118565, incorporated herein by reference.

Embodiments

1. The compound of formula 1, or a pharmaceutically acceptable salt thereof:

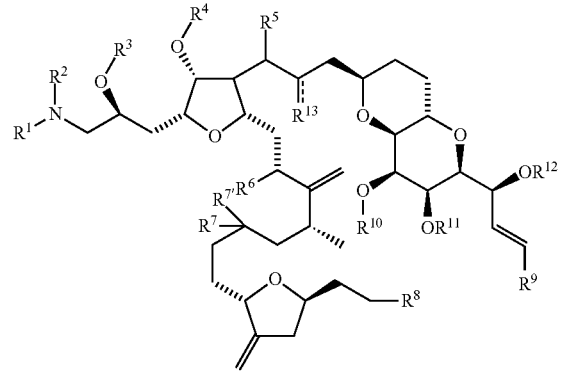

1 wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —$SO_2$(p-tolyl), wherein p-tolyl is —($C_6H_4$)—$CH_3$, with the —$CH_3$ at the para-position;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group;

$R^9$ is a halide or a sulfonate;

or $R^8$ and $R^9$ together form —C(=O)— or —CH($OR^{20}$)—; wherein $R^{20}$ is H or an alcohol protecting group;

$R^{10}$, $R^{11}$ and $R^{12}$ each independently is H or an alcohol protecting group;

----- is a single or double bond; and $R^{13}$ is =O or —$OR^{21}$, wherein $R^{21}$ is H or an alcohol protecting group.

2. The compound according to embodiment 1, or a pharmaceutically acceptable salt thereof, wherein the compound has the structure of formula 1a:

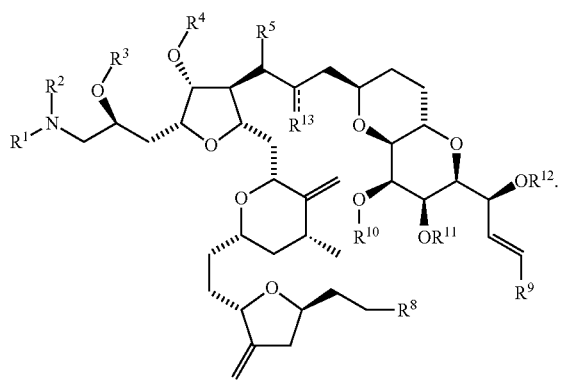

1a

3. The compound according to embodiment 1 or 2, wherein $R^{10}$, $R^{11}$ or $R^{12}$ is an alcohol protecting group.

4. The compound according to embodiment 1 or 2, wherein $R^{10}$, $R^{11}$ or $R^{12}$ is a silyl protecting group.

5. The compound according embodiment 3, wherein $R^{10}$, $R^{11}$ or $R^{12}$ is tert-butyldimethyl silyl (TBS).

6. The compound according to any one of embodiments 1 to 5, wherein $R^{13}$ is =O.

7. The compound according to any one of embodiments 1 to 6, wherein $R^9$ is I.

8. The compound according to any one of embodiments 1 to 7, wherein $R^8$ is —C(=O)H.

9. The compound according to any one of embodiments 1 to 6, wherein $R^8$ and $R^9$ together form —C(=O)—.

10. The compound of formula 2, or a pharmaceutically acceptable salt thereof:

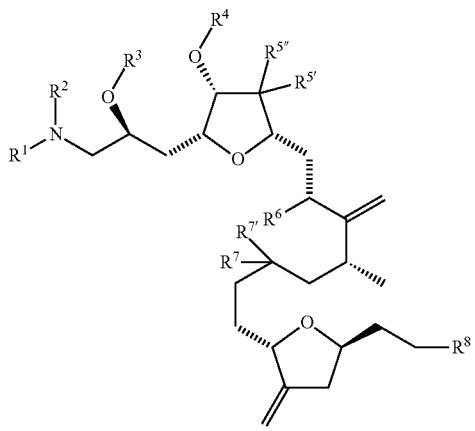

2 wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

one of $R^{5'}$ and $R^{5'''}$ is H and other is —$CH_2SO_2$-(p-tolyl), or $R^{5'}$ and $R^{5'''}$ taken together form =CH—$SO_2$-(p-tolyl), wherein p-tolyl is —($C_6H_4$)—$CH_3$, with the —$CH_3$ at the para-position;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group.

11. The compound according to embodiment 10, or a pharmaceutically acceptable salt thereof, wherein the compound has the structure of formula 2a:

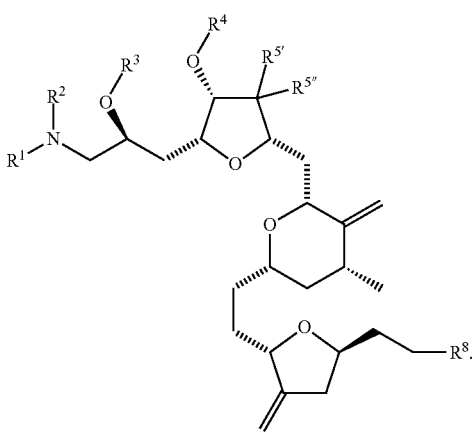

2a

12. The compound according to any one of embodiments 1, 2, 3, 4, 5, 6, 7, 10 and 11, wherein $R^8$ is —$CH_2OR^{18}$, wherein $R^{18}$ is H or an alcohol protecting group.

13. The compound according to embodiment 12, wherein $R^{18}$ is tert-butyldiphenyl silyl (TBDPS).

14. The compound of formula 5, or a salt thereof:

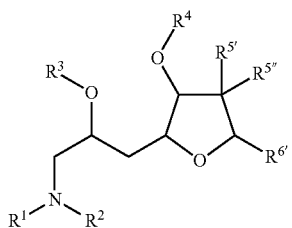

5 wherein, $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl, $C_{1-3}$ haloalkyl or an alcohol protecting group;

one of $R^{5'}$ and $R^{5''}$ is H and the other is —CH$_2$SO$_2$-(p-tolyl), or $R^{5'}$ and $R^{5''}$ taken together form =CH—SO$_2$-(p-tolyl), wherein p-tolyl is —(C$_6$H$_4$)—CH$_3$, with the —CH$_3$ at the para-position;

$R^{6'}$ is —CH$_2$—CH=CR$^{29}$R$^{29'}$, —CH$_2$—CH(OR$^{26}$)—CH(OR$^{26}$)R$^{29}$, —CH$_2$C(=O)—R$^{25}$ or —CH$_2$—CH$_2$—O—R$^{26}$, wherein $R^{29}$ and $R^{29'}$ each independently is H or a hydrocarbon, the hydrocarbon optionally having one or more heteroatoms;

$R^{25}$ is H or OR$^{27}$, wherein $R^{27}$ is H or a hydrocarbon, the hydrocarbon optionally having one or more heteroatoms;

each $R^{26}$ independently is H or an alcohol protecting group.

15. The compound according to embodiment 14, or a salt thereof, wherein the compound has the structure of formula 5a:

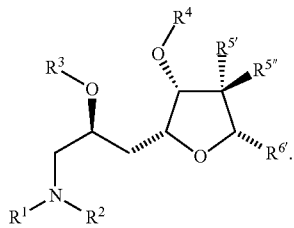

5a

16. The compound according to embodiment 14 or 15, wherein $R^{5'}$ is H and $R^{5''}$ is —CH$_2$SO$_2$-(p-tolyl), wherein p-tolyl is —(C$_6$H$_4$)—CH$_3$, with the —CH$_3$ at the para-position.

17. The compound according to any one of embodiments 14 to 16, wherein $R^{6'}$ is —CH$_2$C(=O)—R$^{25}$, and wherein $R^{25}$ is H or OR$^{27}$, wherein $R^{27}$ is H or a hydrocarbon, the hydrocarbon optionally having one or more heteroatoms.

18. The compound according to any one of embodiments 1 to 17, wherein $R^3$ is H, a silyl group, an acyl group or an alkoxycarbonyl group.

19. The compound according to any one of embodiments 1 to 18, wherein $R^1$ and $R^2$ each independently is H, a silyl group, an acyl group, a sulfonyl group or an alkoxycarbonyl group, and at least one of $R^1$ and $R^2$ is other than H.

20. The compound according to any one of embodiments 1 to 17, wherein $R^3$ and one of $R^1$ and $R^2$ together form —C(=O)—, and other $R^1$ or $R^2$ is H, a silyl group, an acyl group or an alkoxycarbonyl group.

21. The compound according to any one of embodiments 1 to 20, wherein $R^4$ is $C_{1-3}$ alkyl group.

22. The compound according to any one of embodiments 1 to 20, wherein $R^4$ is benzyl.

23. A process for preparation of a compound of formula 3, or a pharmaceutically acceptable salt thereof, the process comprising

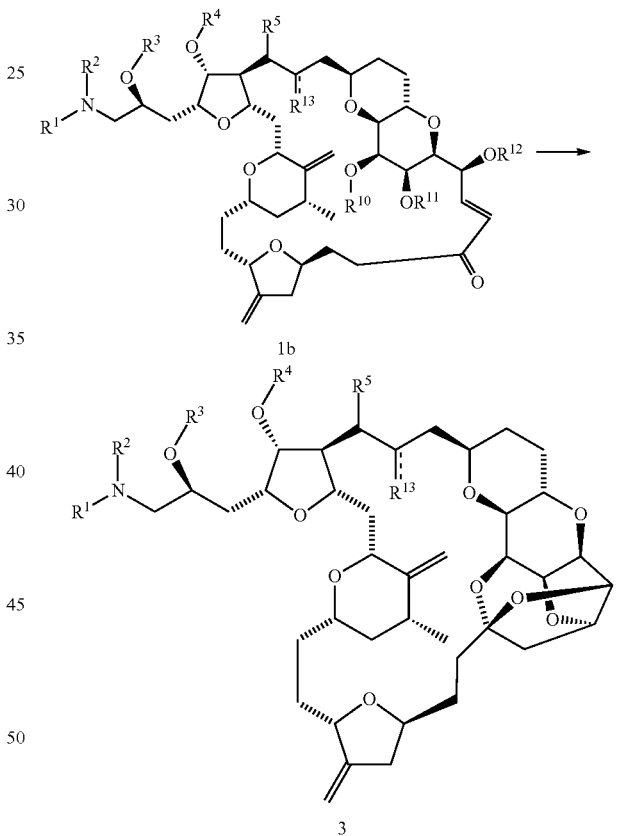

performing an intramolecular cyclization reaction on a compound of formula 1b to form the compound of formula 3, wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —$SO_2$(p-tolyl), wherein p-tolyl is —$(C_6H_4)$—$CH_3$, with the —$CH_3$ at the para-position;

$R^{10}$, $R^{11}$ and $R^{12}$ each independently is H or an alcohol protecting group;

----- is a single or double bond; and $R^{13}$ is =O or —$OR^{21}$, wherein $R^{21}$ is H or an alcohol protecting group.

24. A process for preparation of a compound of formula 1, or a pharmaceutically acceptable salt thereof, the process comprising:

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

$R^5$ is H or —$SO_2$(p-tolyl), wherein p-tolyl is —$(C_6H_4)$—$CH_3$, with the —$CH_3$ at the para-position;

$R^6$ is $OR^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

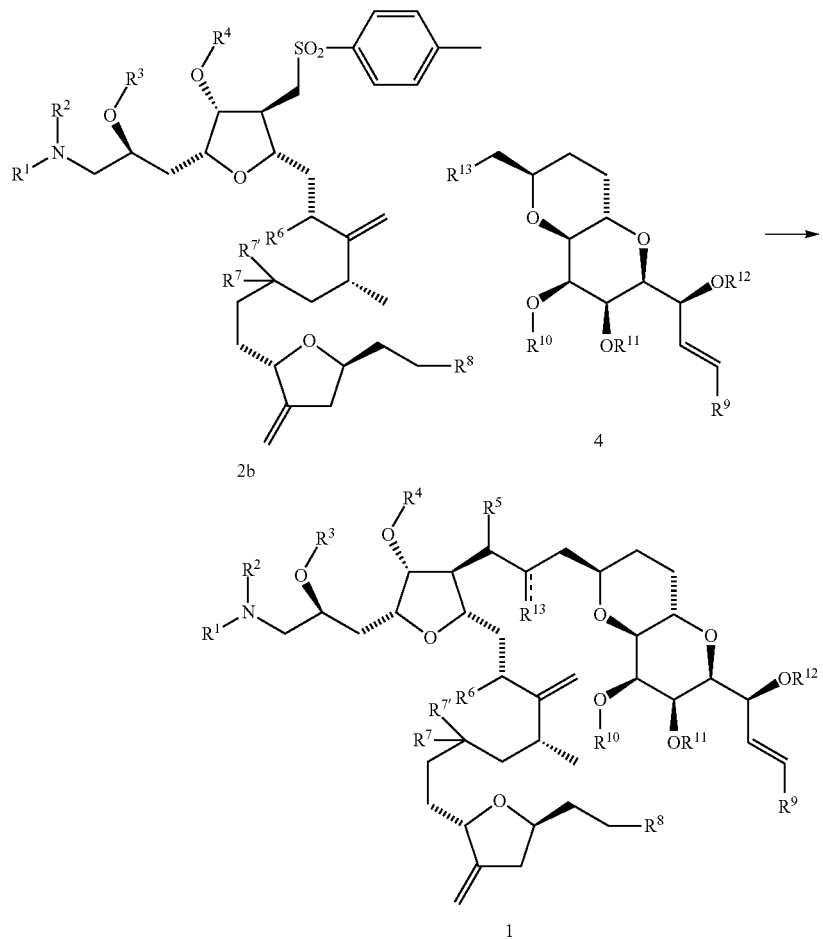

coupling a compound of formula 2b with a compound of formula 4 to form the compound of formula 1; wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

$R^8$ is —C(=O)$R^{17}$ or —$CH_2OR^{18}$; wherein $R^{17}$ is H or $OR^{19}$, wherein $R^{19}$ is H or a hydrocarbon, the hydrocarbon optionally having one or more heteroatoms;

$R^{18}$ is H or an alcohol protecting group;

$R^9$ is a halide or a sulfonate;

or $R^8$ and $R^9$ together form —C(=O)— or —CH($OR^{20}$)—; wherein $R^{20}$ is H or an alcohol protecting group;

$R^{10}$, $R^{11}$ and $R^{12}$ each independently is H or an alcohol protecting group;

----- is a single or a double bond;

$R^{13}$ is =O or —$OR^{21}$, wherein $R^{21}$ is H or an alcohol protecting group; and $R^{13'}$ is —C(=O)$R^{22}$, wherein $R^{22}$ is H or O$R^{23}$, wherein $R^{23}$ is H or a hydrocarbon, the hydrocarbon optionally having one or more heteroatoms.

25. The process according to embodiment 24, wherein the coupling reaction is performed using a base.

26. The process according to embodiment 25, wherein the base is n-butyllithium.

27. A process for preparation of compound of formula 2, or a pharmaceutically acceptable salt thereof, the process comprising:

5b

6

2 coupling a compound of formula 5b with a compound of formula 6, wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

one of $R^{5'}$ and $R^{5''}$ is H and the other is —CH$_2$SO$_2$-(p-tolyl), or $R^{5'}$ and $R^{5''}$ taken together form =CH—SO$_2$-(p-tolyl), wherein p-tolyl is —(C$_6$H$_4$)—CH$_3$, with the —CH$_3$ at the para-position;

$R^6$ is O$R^{16}$, wherein $R^{16}$ is H or an alcohol protecting group;

$R^7$ and $R^{7'}$ together form a =O or a protected geminal diol, or one of $R^7$ and $R^{7'}$ is H and the other is a leaving group or a functional group that can be converted into a leaving group;

or $R^6$ and one of $R^7$ and $R^{7'}$ together form —O—, and the other $R^7$ or $R^{7'}$ is H;

$R^{6'}$ is —CH$_2$C(=O)$R^{25}$ or —CH$_2$CH$_2$O$R^{26}$; wherein $R^{25}$ is H or O$R^{27}$, wherein $R^{27}$ is H or a hydrocarbon, the hydrocarbon optionally having one or more heteroatoms;

$R^{26}$ is H or an alcohol protecting group;

$R^8$ is —C(=O)$R^{17}$ or —CH$_2$O$R^{18}$; wherein $R^{17}$ is H or O$R^{19}$, wherein $R^{19}$ is H or a hydrocarbon, the hydrocarbon optionally having one or more heteroatoms;

$R^{18}$ is H or an alcohol protecting group; and $R^{24}$ is a halide or a sulfonate.

28. The process according to embodiment 27, wherein $R^{6'}$ is —CH$_2$C(=O)H, and the coupling reaction is performed using a nickel/chromium catalyst.

29. A process for preparation of the compound of formula 5, or a salt thereof, the process comprising:

converting the terminal alcohol of the compound of formula 7 into an amine or substituted amine to form the compound of formula 5

7

5 wherein $R^1$ and $R^2$ each independently is H, a silyl group, an acyl group, a sulfonyl group or an alkoxycarbonyl group; and $R^3$ is H or an alcohol protecting group;

or $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms; and the remaining of $R^1$ and $R^2$ is H, a silyl group, an acyl group, a sulfonyl group or an alkoxycarbonyl group;

or one of $R^1$ and $R^2$ is absent and the other $R^1$ or $R^2$ together with the nitrogen atom to which it is attached form an azide, and $R^3$ is H or an alcohol protecting group;

$R^4$ is H, $C_{1-3}$ alkyl or $C_{1-3}$ haloalkyl or an alcohol protecting group;

one of $R^{5'}$ and $R^{5''}$ is H and the other is —CH$_2$SO$_2$-(p-tolyl), or $R^{5'}$ and $R^{5''}$ taken together form =CH—SO$_2$-(p-tolyl), wherein p-tolyl is —(C$_6$H$_4$)—CH$_3$, with the —CH$_3$ at the para-position;

$R^{6'}$ is —CH$_2$—CH=C$R^{29}R^{29'}$, —CH$_2$—CH(O$R^{26}$)—CH(O$R^{26}$)$R^{29}$, —CH$_2$C(=O)—$R^{25}$ or —CH$_2$—CH$_2$—O—$R^{26}$, wherein $R^{29}$ and $R^{29'}$ each independently is H or a hydrocarbon, the hydrocarbon optionally having one or more heteroatoms;

$R^{25}$ is H or O$R^{27}$, wherein $R^{27}$ is H or a hydrocarbon, the hydrocarbon optionally having one or more heteroatoms; and each $R^{26}$ independently is H or an alcohol protecting group.

30. A process for preparation of Eribulin, containing the process as defined in any one of embodiments 23 to 29.

31. A process for preparation an analog of halichondrin, containing the process as defined in any one of embodiments 23 to 29.

Certain adaptations and modifications of the described embodiments can be made. Therefore, the above discussed embodiments are considered to be illustrative and not restrictive.

The invention claimed is:

1. The compound of formula 1:

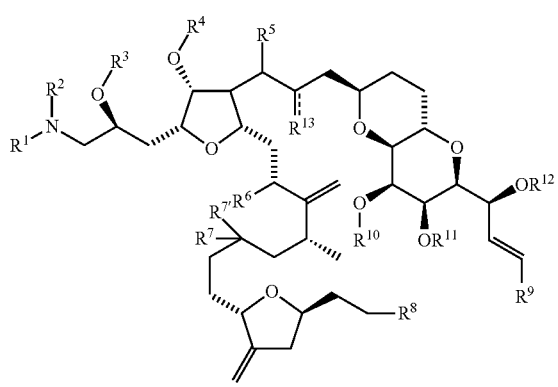

1 wherein
  $R^1$ and $R^2$ each independently is H, a silyl group, an acyl group, a sulfonyl group or an alkoxycarbonyl group; or one of $R^1$ and $R^2$ is absent and the other $R^1$ or $R^2$ together with the nitrogen atom to which it is attached form an azide;
  $R^3$ is H or an alcohol protecting group; or
  $R^3$ and one of $R^1$ and $R^2$ together form —C(=O)—, —C(=O)—C(=O)— or —C($R^{14}$)($R^{15}$)—, wherein $R^{14}$ and $R^{15}$ each independently is H or a hydrocarbon, the hydrocarbon optionally having one or more heteroatoms;
  $R^4$ is H, $C_{1-3}$ alkyl or $C_{1-3}$ haloalkyl or an alcohol protecting group;
  $R^5$ is —$SO_2$(p-tolyl), wherein p-tolyl is —($C_6H_4$)—$CH_3$, with the —$CH_3$ at the para-position;
  $R^6$ is $OR^{16}$, wherein $R^{16}$ is H or an alcohol protecting group;
  $R^7$ and $R^{7'}$ together form a =O or a protected geminal diol, or one of $R^7$ and $R^{7'}$ is H and the other is a leaving group or a functional group that can be converted into a leaving group; or
  $R^6$ and one of $R^7$ and $R^{7'}$ together form —O—, and the other $R^7$ or $R^{7'}$ is H;
  $R^8$ is —C(=O)$R^{17}$ or —$CH_2OR^{18}$, wherein
    $R^{17}$ is H or $OR^{19}$, wherein $R^{19}$ is H or a hydrocarbon, the hydrocarbon optionally having one or more heteroatoms;
    $R^{18}$ is H or an alcohol protecting group;
  $R^9$ is a halide or a sulfonate; or
  $R^8$ and $R^9$ together form —C(=O)— or —CH($OR^{20}$)—, wherein $R^{20}$ is H or an alcohol protecting group;
  $R^{10}$, $R^{11}$ and $R^{12}$ each independently is H or an alcohol protecting group;
  ----- is a single or double bond; and
  $R^{13}$ is =O or —$OR^{21}$, wherein $R^{21}$ is H or an alcohol protecting group.

2. The compound according to claim 1, wherein the compound has the structure of formula 1a:

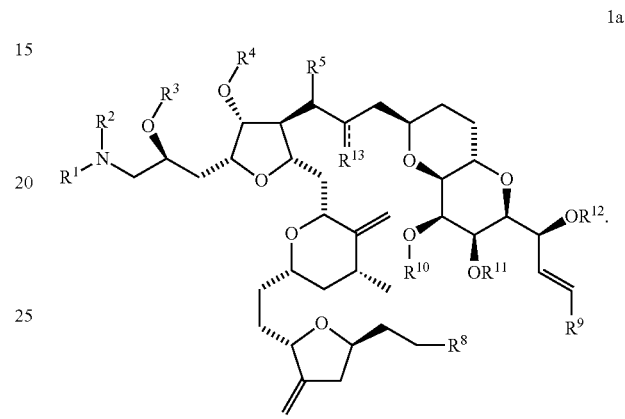

1a

3. The compound according to claim 1, wherein $R^{10}$, $R^{11}$ or $R^{12}$ is an alcohol protecting group, or a silyl protecting group.

4. The compound according to claim 3, wherein the protecting group is tert-butyldimethyl silyl (TBS).

5. The compound according to claim 1, wherein $R^{13}$ is =O.

6. The compound according to claim 1, wherein $R^9$ is I.

7. The compound according to claim 1, wherein $R^8$ is —C(=O)H.

8. The compound according to claim 1, wherein $R^8$ and $R^9$ together form —C(=O)—.

9. The compound according to claim 1, wherein $R^8$ is —$CH_2OR^{18}$, wherein $R^{18}$ is H or an alcohol protecting group.

10. The compound according to claim 9, wherein the protecting group is tert-butyldiphenyl silyl (TBDPS).

11. The compound according to claim 1, wherein $R^3$ is H, a silyl group, an acyl group or an alkoxycarbonyl group.

12. The compound according to claim 1, wherein $R^1$ and $R^2$ each independently is H, a silyl group, an acyl group, a sulfonyl group or an alkoxycarbonyl group, and at least one of $R^1$ and $R^2$ is other than H.

13. The compound according to claim 1, wherein $R^3$ and one of $R^1$ and $R^2$ together form —C(=O)—, and other $R^1$ or $R^2$ is H, a silyl group, an acyl group or an alkoxycarbonyl group.

14. The compound according to claim 1, wherein $R^4$ is $C_{1-3}$ alkyl group or benzyl.

* * * * *